United States Patent
Kataoka et al.

(10) Patent No.: US 8,941,079 B2
(45) Date of Patent: Jan. 27, 2015

(54) LIGHT IRRADIATION DEVICE AND LIGHT MEASUREMENT DEVICE

(75) Inventors: Takuji Kataoka, Hamamatsu (JP); Taira Ito, Hamamatsu (JP)

(73) Assignee: Hamamatsu Photonics K.K., Hamamatsu-shi, Shizuoka (JP)

(*) Notice: Subject to any disclaimer, the term of this patent is extended or adjusted under 35 U.S.C. 154(b) by 181 days.

(21) Appl. No.: 13/146,212

(22) PCT Filed: Jan. 26, 2010

(86) PCT No.: PCT/JP2010/050968
§ 371 (c)(1),
(2), (4) Date: Jul. 26, 2011

(87) PCT Pub. No.: WO2010/109939
PCT Pub. Date: Sep. 30, 2010

(65) Prior Publication Data
US 2011/0284766 A1    Nov. 24, 2011

(30) Foreign Application Priority Data

Mar. 26, 2009 (JP) ................................ 2009-076595
Mar. 26, 2009 (JP) ................................ 2009-076601

(51) Int. Cl.
*F21V 9/16* (2006.01)
*G01N 21/64* (2006.01)

(52) U.S. Cl.
CPC ................................ *G01N 21/6452* (2013.01)
USPC ...................................... 250/458.1; 356/445

(58) Field of Classification Search
CPC  G01N 21/0303; G01N 21/6452; G01N 21/65
USPC ......... 250/458.1, 432 R, 459.1, 461.1–461.2; 356/445
See application file for complete search history.

(56) References Cited

U.S. PATENT DOCUMENTS 6,104,484 A * 8/2000 Nagata et al. ................. 356/246
6,538,735 B1   3/2003 Duebendorfer et al.
(Continued)

FOREIGN PATENT DOCUMENTS

CN      1769933      5/2006
CN      1890553      1/2007
(Continued)

OTHER PUBLICATIONS

Daniel Filippini et al., "Microplate based biosensing with a computer screen aided technique" Biosensors and Bioelectronics, vol. 19, No. 1, Dec. 31, 2003, p. 35-p. 41.

*Primary Examiner* — David Porta
*Assistant Examiner* — Taeho Jo
(74) *Attorney, Agent, or Firm* — Drinker Biddle & Reath LLP

(57) ABSTRACT

The present invention relates to a light irradiation apparatus and the like which can reduce background light noise from a plurality of wells provided on a microplate. The light irradiation apparatus comprises a microplate, a light guiding member, and a light source apparatus. The light guiding member includes a plurality of light emitting units provided on a main surface in correspondence with the plurality of wells. Each light emitting unit includes depressions each having an opening on the main surface. Measurement light from the light source apparatus is inputted from a side surface, refracted and reflected at the side surface of each depression, and then outputted from the opening of each depression.

32 Claims, 19 Drawing Sheets

(56) References Cited

U.S. PATENT DOCUMENTS

| | | | |
|---|---|---|---|
| 6,728,429 B1* | 4/2004 | Melman et al. | 385/12 |
| 7,102,754 B2* | 9/2006 | Ohtsuka et al. | 356/445 |
| 7,342,663 B2* | 3/2008 | Matsushita et al. | 356/445 |
| 2003/0127609 A1* | 7/2003 | El-Hage et al. | 250/574 |
| 2005/0218338 A1* | 10/2005 | Wulf et al. | 250/458.1 |
| 2007/0008536 A1* | 1/2007 | Mitani et al. | 356/417 |
| 2007/0211254 A1* | 9/2007 | Matsushita et al. | 356/445 |
| 2010/0243916 A1* | 9/2010 | Maurer et al. | 250/459.1 |

FOREIGN PATENT DOCUMENTS

| | | |
|---|---|---|
| JP | 10-197449 | 7/1998 |
| JP | 10-281994 | 10/1998 |
| JP | 2002-139418 | 5/2002 |
| JP | 2003-287493 | 10/2003 |
| JP | 2005-274355 | 10/2005 |
| JP | 2007-108146 | 4/2007 |
| WO | 2005/054826 | 6/2005 |

* cited by examiner

Fig.2
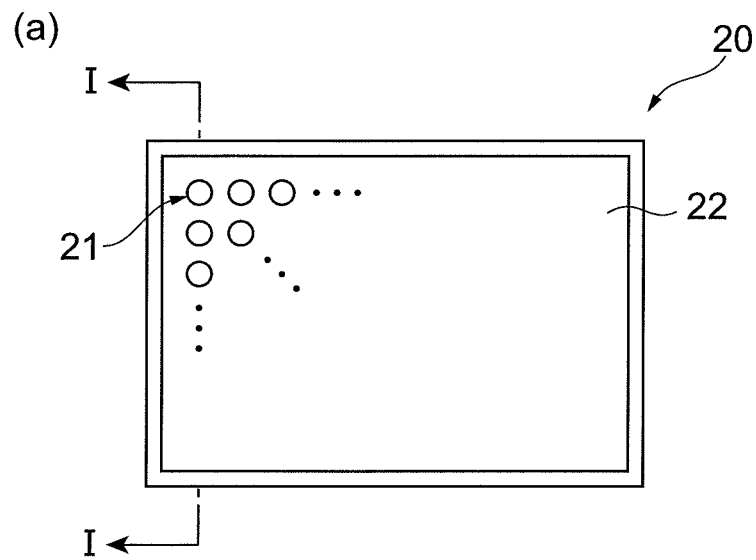
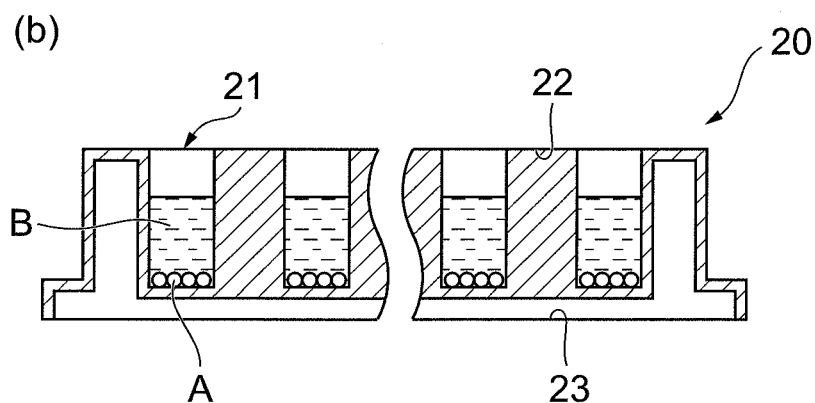
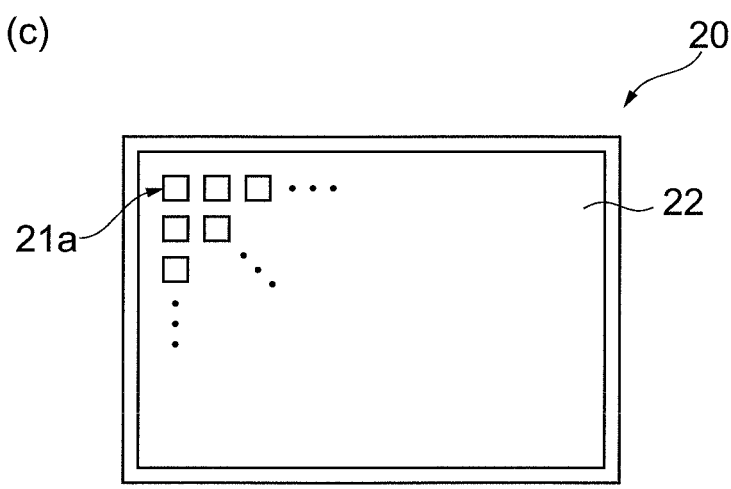

Fig.3
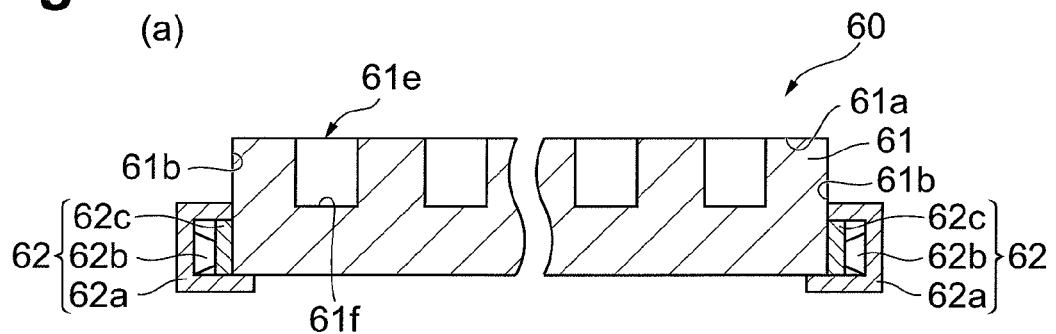
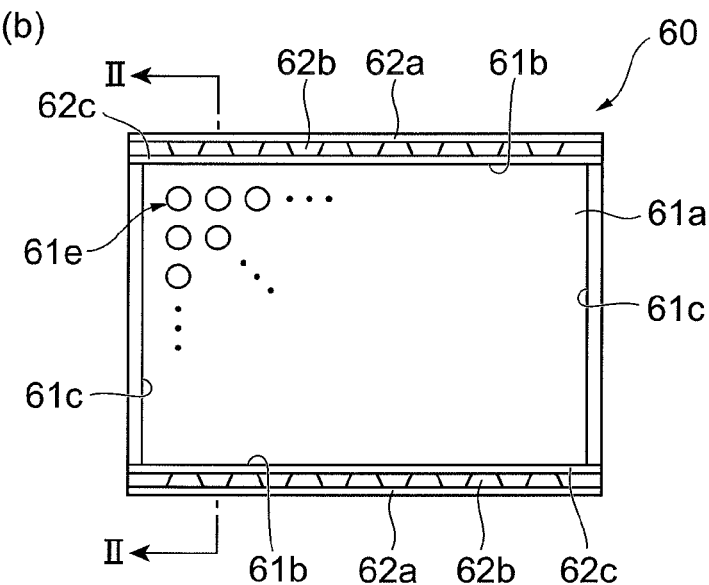
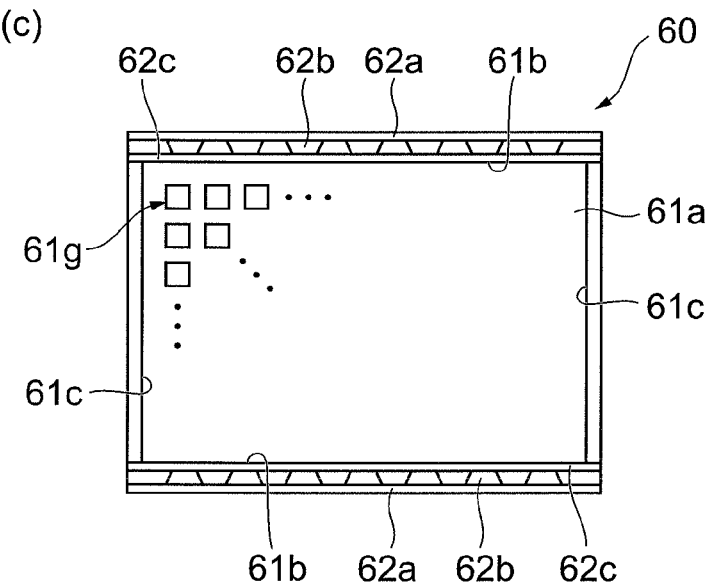

Fig.6
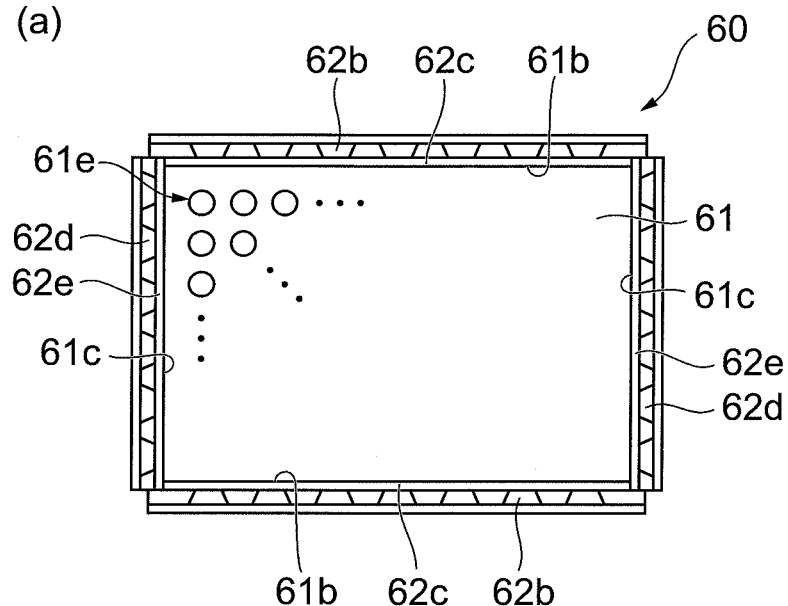
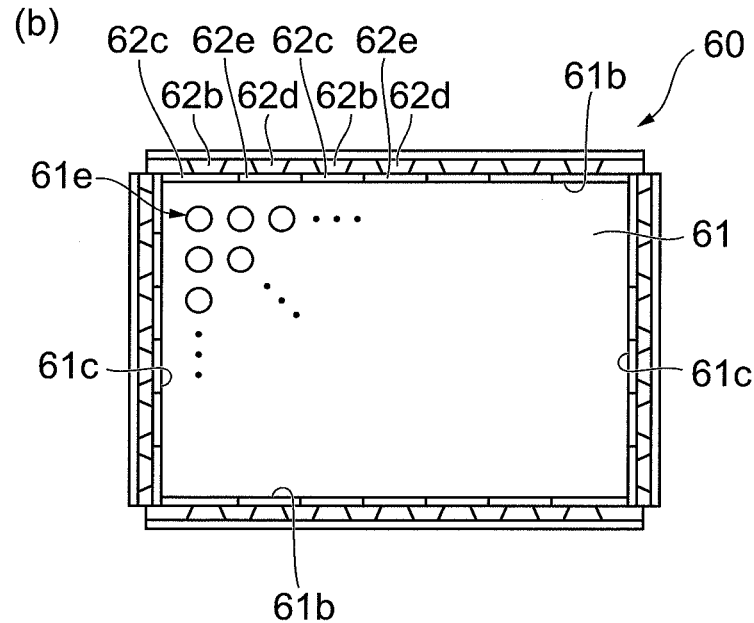

Fig.7
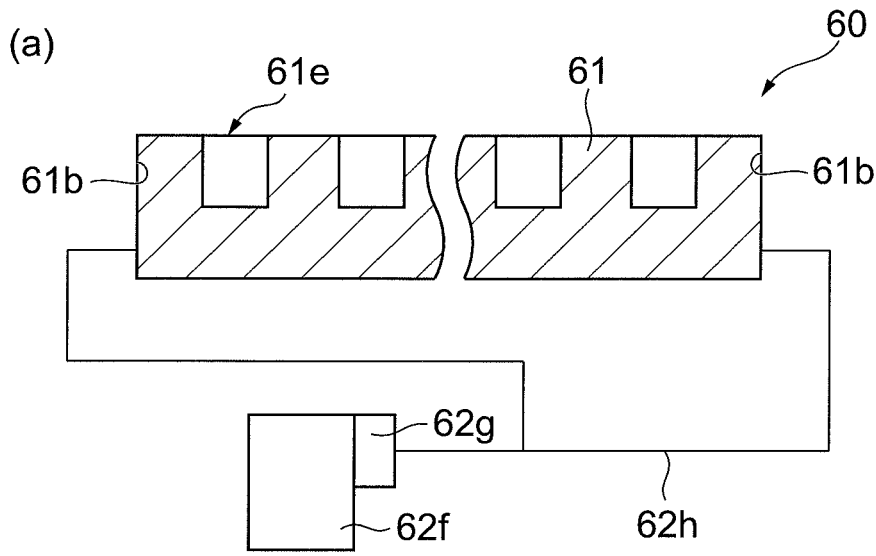
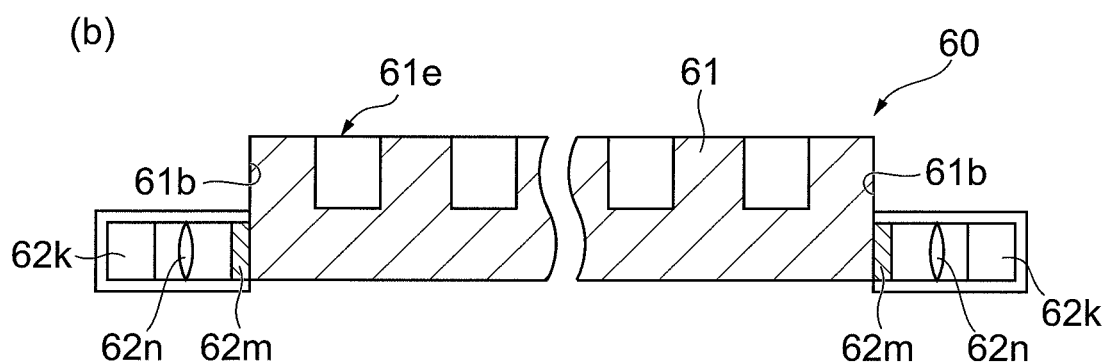
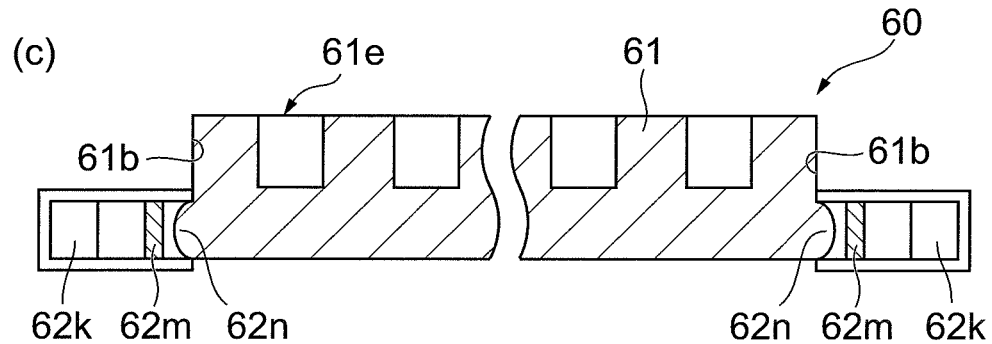

Fig.14
(a)
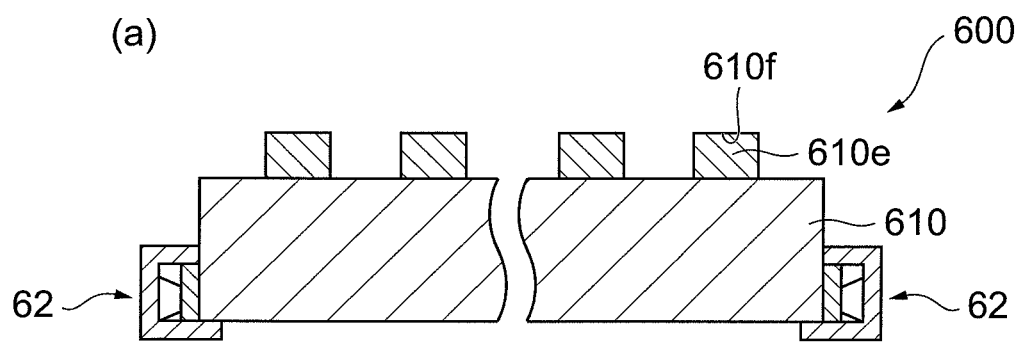
(b)
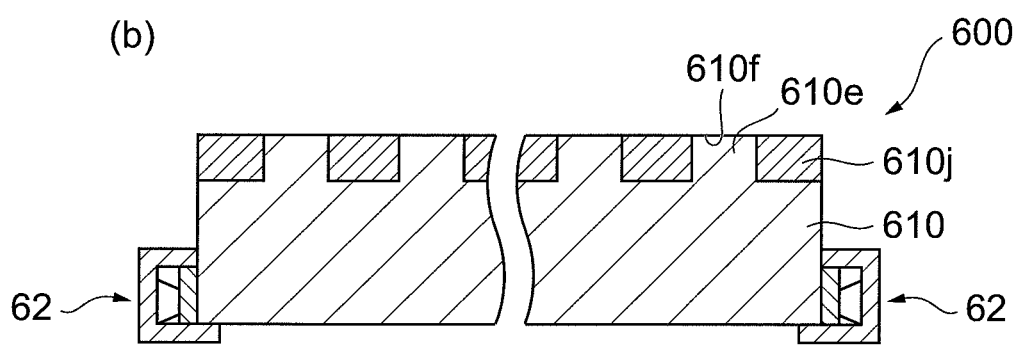
(c)
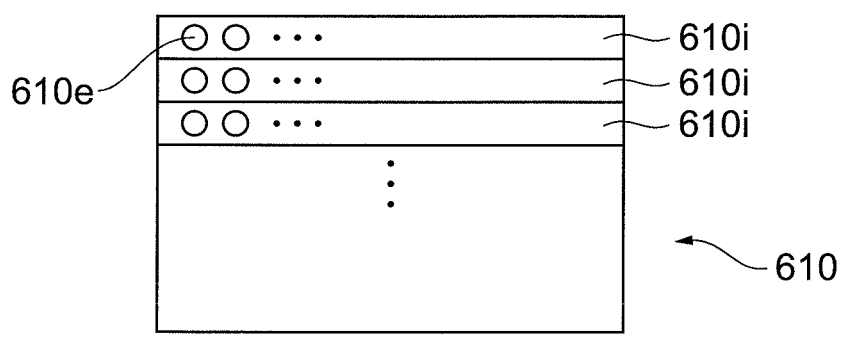

Fig.15
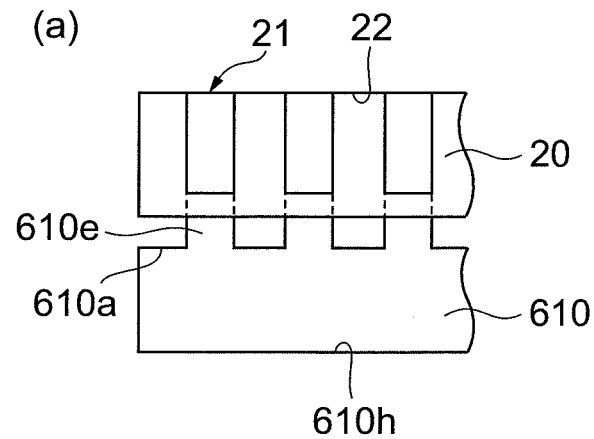
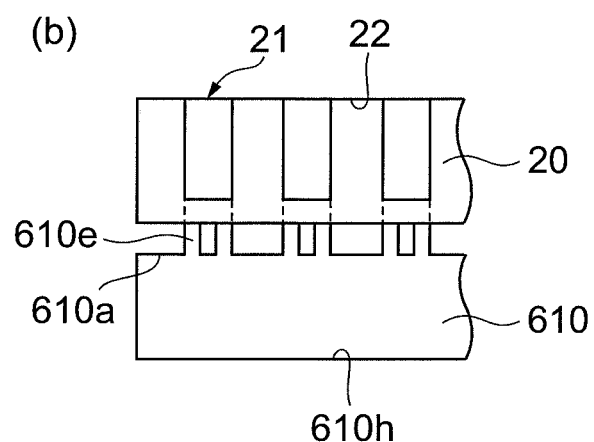
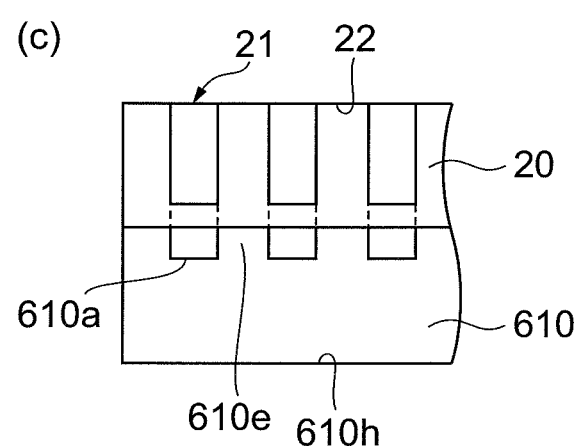

Fig.16
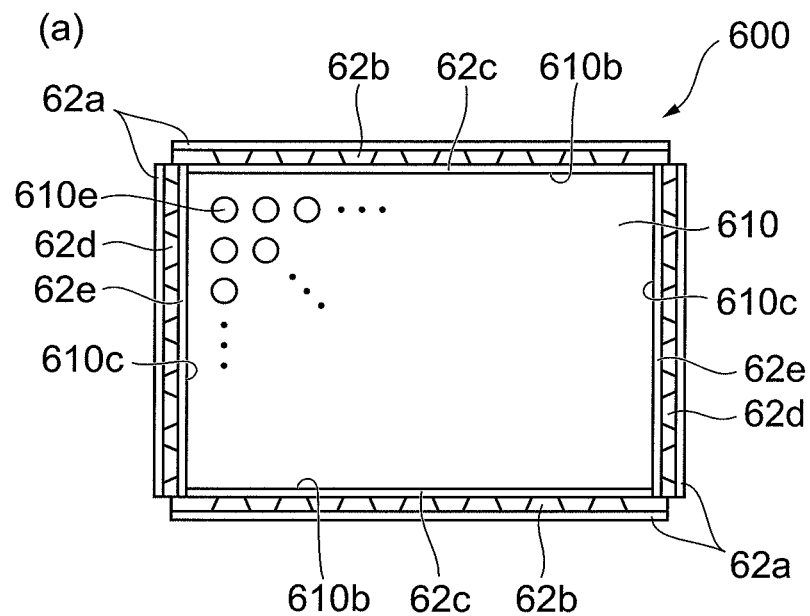
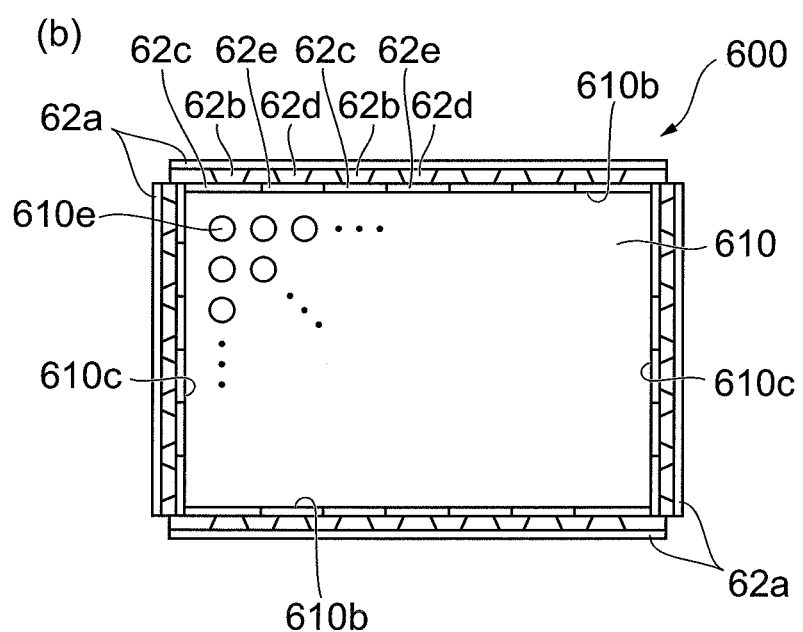

Fig.17
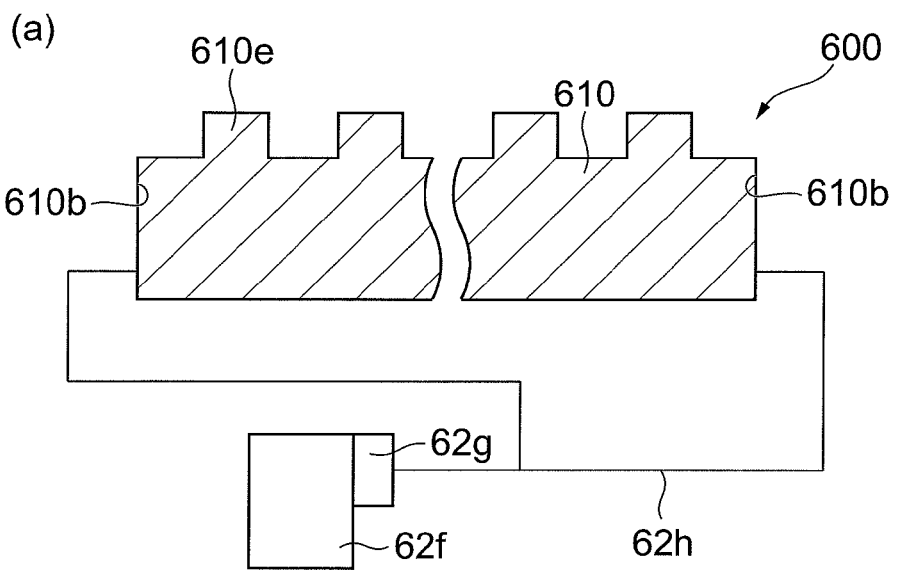
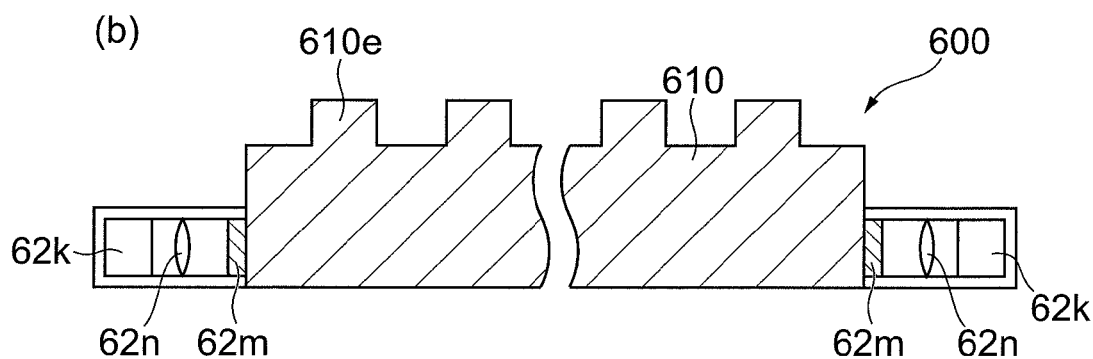
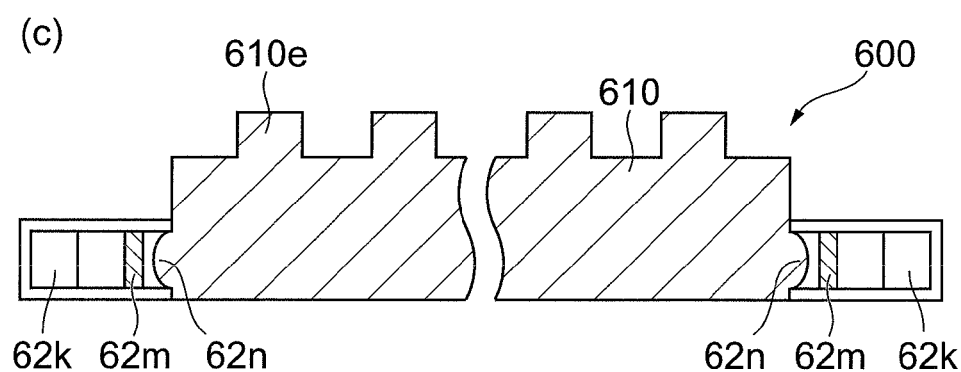

Fig.19
(a)
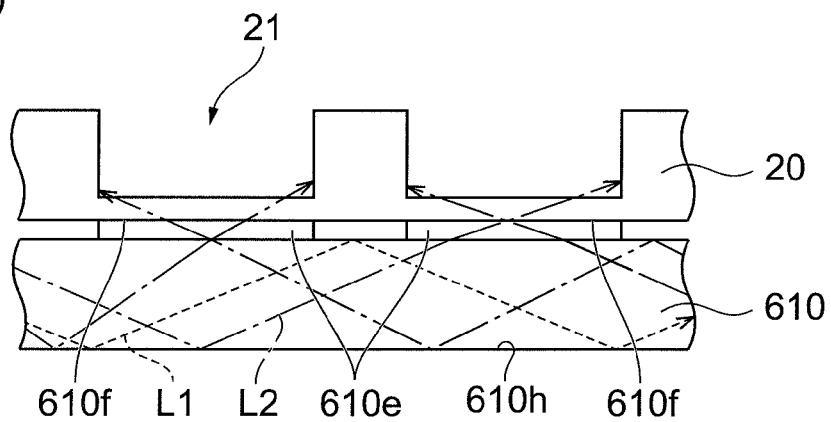
(b)
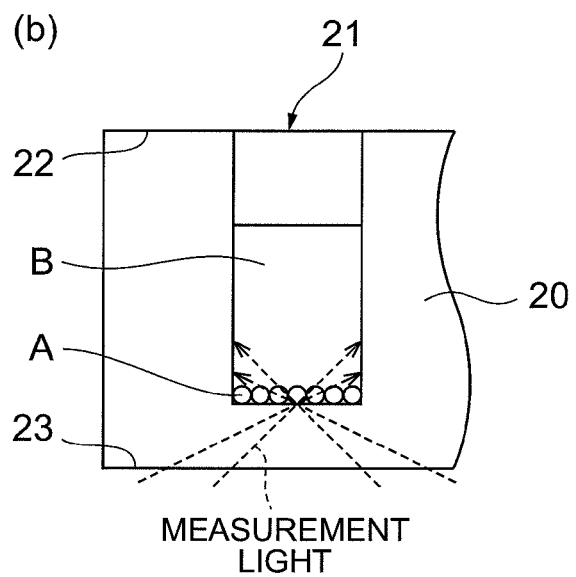
MEASUREMENT LIGHT
(c)
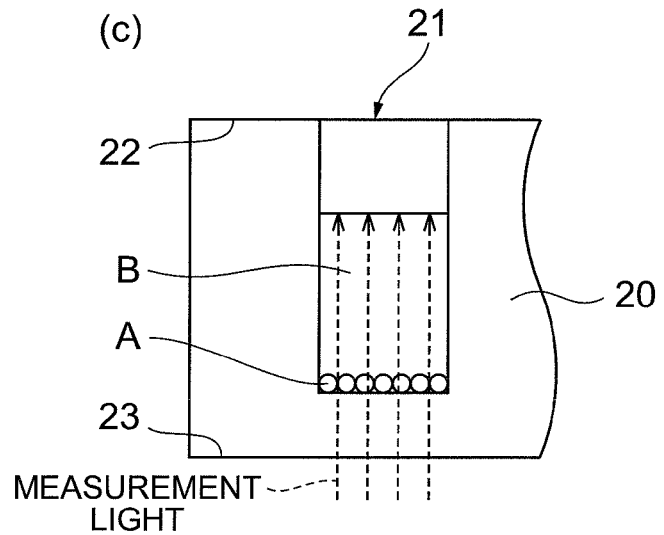
MEASUREMENT LIGHT

LIGHT IRRADIATION DEVICE AND LIGHT MEASUREMENT DEVICE

TECHNICAL FIELD

The present invention relates to a light irradiation apparatus for irradiating a microplate with measurement light, and a light measurement apparatus comprising the light irradiation apparatus and the microplate to enable measurement of fluorescence from an object to be measured, or the like.

BACKGROUND ART

Conventionally, technology described in Patent Documents 1 to 3, for example, is known as technology which irradiates each of a plurality of wells two-dimensionally arranged on the main surface of a microplate with measurement light (pumping light). With the technology described in Patent Document 1, the measurement light is irradiated from the back surface of the microplate to the well corresponding in parallel with the depth direction of the well. Solution of culture fluid, fluorescence indicator, evaluation compounds or the like, and the object to be measured such as cells are injected into each well arranged on the microplate.

CITATION LIST

Patent Document

Patent Document 1: Japanese Patent Application Laid-Open No. 2007-108146
Patent Document 2: Japanese Patent Application Laid-Open No. 10-197449
Patent Document 3: Japanese Patent Application Laid-Open No. 10-281994

SUMMARY OF INVENTION

Problems that the Invention is to Solve

The present inventors have examined the above prior art, and as a result, have discovered the following problems.

That is, in the irradiation method of measurement light described in Patent Document 1, the measurement light is irradiated to a well corresponding in parallel with the depth direction of the well. Therefore, a large amount of the measurement light is irradiated not only to the object to be measured but also to the solution. In this case, there is a problem that background light noise from the solution in each well becomes relatively large.

The present invention has been developed to eliminate the problems described above. It is an object of the present invention to provide a light irradiation apparatus comprising a structure for effectively reducing background light noise from a plurality of wells arranged on a microplate, and a light measurement apparatus including the light irradiation apparatus and the microplate.

Solution to Problem

A light irradiation apparatus according to the present invention irradiates a microplate having a main surface on which a plurality of wells is two-dimensionally arranged to accommodate an object to be measured and a back surface opposing the main surface, with measurement light from the back surface of the microplate. The light irradiation apparatus includes a light source and a light guiding member. The light source outputs measurement light to be irradiated to each of the plurality of wells from the back surface side of the microplate. The light guiding member is a member through which the measurement light outputted from the light source propagates, and has a structure for irradiating each well of the microplate with the measurement light. Specifically, the light guiding member has a main surface directly facing the back surface of the microplate, a back surface opposing the main surface, and a side surface intersecting the main and back surfaces. The side surface functions as a light incidence plane onto which the measurement light from the light source is incident. In addition, a light measurement apparatus according to the present invention comprises the light irradiation apparatus having a structure described above, and the microplate arranged so that the back surface directly faces the main surface of the light guiding member in the light irradiation apparatus.

Particularly, the light guiding member has a plurality of light emitting units arranged on the main surface thereof, each corresponding to each of the plurality of wells of the microplate. These light emitting units control the direction of emission of the measurement light to prevent the measurement light having propagated through the light guiding member from being incident on the back surface of the microplate from a perpendicular direction thereof. That is, each light emitting unit functions to scatter the measurement light traveling from each light emitting unit toward a corresponding well of the microplate. In other words, measurement light is refracted and reflected on the surface of each light emitting unit, and irradiated toward the back surface of the microplate, on a well to which the refracted light component and the reflected light component correspond. By such a configuration, the measurement light component perpendicularly incident on the back surface can be significantly reduced, among the measurement light incident from the back surface of the microplate. Therefore, background light noise from each well occurring in response to measurement light irradiation is effectively reduced.

For example, each of the light emitting units arranged on the main surface of the light guiding member includes one or more depressions each having an opening on the main surface and extending from the main surface toward the back surface of the light guiding member. In this case, the light guiding member can be arranged so that the back surface of the microplate (bottom surface of each well) and the opening of each depression are opposite to each other. In addition, the measurement light, inputted into the light guiding member from the side surface thereof, is refracted and reflected at the side surface of each depression, and then outputted from the opening of each depression.

In the light measurement apparatus comprising the light irradiation apparatus having a light guiding member with depressions formed on its main surface as light irradiation units, and a microplate, when measurement light is incident in the light guiding member from the side surface of the light guiding member, the measurement light is refracted and reflected at the side surface of each depression, and incident on the bottom surface of a corresponding well from the opening of each depressions.

In accordance with the light irradiation apparatus and the light measurement apparatus to which depressions are applied as light emitting units as described above, the measurement light is refracted and reflected at the side surface of each depression, and emitted from the opening of each depression. In other words, the traveling direction of the measurement light reaching each corresponding well is inclined against the depth direction of the well. Accordingly, the amount of the measurement light irradiated on solution of culture fluid, fluorescence indicator, evaluation compounds or the like accommodated in each well of the microplate relatively decreases. Therefore, background light noise from each well of the microplate occurring due to irradiation of the measurement light on the solution in each well can be effectively reduced.

It is preferred that each of the depressions arranged on the main surface of the light guiding member as the light emitting unit is a columnar depression. In this case, random scattering of light may easily be induced inside each depression because the side surface of each depression does not have a corner. Therefore, unevenness in the irradiation of measurement light on each well of the microplate can be reduced.

It is preferred that each of the depressions arranged on the main surface of the light guiding member as the light emitting unit has a flat bottom surface. In this case, a part of the measurement light reaching the flat bottom surface of each depression after having propagated through the light guiding member is totally reflected at the bottom surface of each depression. Therefore, the measurement light which is parallel to the depth direction of the well is reduced.

In addition, it is preferred that the bottom surface of each of the depressions arranged on the main surface of the light guiding member as the light emitting unit is mirror-finished. In this case, most of the measurement light reaching the bottom surface of each depression is totally reflected at the bottom surface of each depression after having propagated through the light guiding member. Therefore, the measurement light which is parallel to the depth direction of the well can be further reduced.

Each of the light emitting units arranged on the main surface of the light guiding member may include one or more protrusions protruding from the main surface of the light guiding member toward the opposite direction of the back surface. In this case, each of the protrusions has an upper surface which is substantially parallel to the main surface of the light guiding member, and the light guiding member can be arranged so that the upper surface of each of the protrusions directly contacts the back surface of the microplate.

In the light measurement apparatus comprising the light irradiation apparatus having the light guiding member with protrusions formed on its main surface as light irradiation units, and the microplate, the light guiding member is arranged so that the upper surface of each protrusion contacts the back surface of the microplate, and the upper surface of each protrusion faces the bottom surface of each well of the microplate. In addition, the measurement light inputted from the side surface of the light guiding member is reflected at the main surface and the back surface of the light guiding member, and inputted from the upper surface of each protrusion onto the bottom surface of each well arranged on the microplate.

In accordance with the light irradiation apparatus and the light measurement apparatus to which depressions are applied as light emitting units as described above, the measurement light inputted from the side surface of the light guiding member is reflected at the main surface and the back surface of the light guiding member, and subsequently reaches each corresponding well of the microplate from the upper surface of each protrusion. In this occasion, the traveling direction of the measurement light reaching the bottom surface of each well is inclined against the depth direction of the well. Therefore, the amount of measurement light irradiated on solution of culture fluid, fluorescence indicator, evaluation compounds or the like accommodated in each well of the microplate is relatively small. Therefore, background light noise from each well of the microplate occurring due to irradiation of the measurement light on the solution in each well can be effectively reduced.

It is preferred that each of the protrusions arranged on the main surface of the light guiding member as the light emitting unit has a higher refractive index than the main body of the light guiding member (a region surrounded by the main surface, the back surface, and the side surface). In this case, it becomes easier for the measurement light to pass from main body of the light guiding member to each protrusion. As a result, a still larger amount of the measurement light can be irradiated onto each of the wells of the microplate.

It is also preferred that the main surface and the back surface of the light guiding member are mirror-finished. In this case, a part of the measurement light inputted into the light guiding member is totally reflected at the main surface and the back surface of the light guiding member. As a result, leakage of the measurement light from the main surface and the back surface of the light guiding member can be effectively suppressed.

In the configuration having a plurality of protrusions arranged on the main surface of the light guiding member as light emitting units, it is preferred that the light irradiation apparatus according to the present invention further comprises a filling member which is filled in the space between the protrusions and has a lower refractive index than each protrusion. In this case, leakage of the measurement light reaching the protrusion after having propagated through the light guiding member, i.e., leakage of the measurement light from the side surface of each protrusion can be effectively suppressed.

Effects of the Invention

In accordance with the light irradiation apparatus and the light measurement apparatus according to the present invention, background light noise from the wells arranged on the microplate is drastically reduced.

BRIEF DESCRIPTION OF THE DRAWINGS

FIG. 2 is a view for explaining a structure of a microplate shown in FIG. 1;

FIG. 3 is a view for explaining a structure of a light irradiation apparatus shown in FIG. 1;

FIG. 6 is a plan view for explaining another structure of the light irradiation apparatus shown in FIG. 1;

FIG. 7 is a cross-sectional view for explaining another structure of the light irradiation apparatus shown in FIG. 1;

FIG. 14 is a view for explaining the another structure of the light irradiation apparatus shown in FIG. 11;

FIG. 15 is a view for explaining the positional relation between wells of the microplate shown in FIG. 11 and protrusions of the light guiding member;

FIG. 16 is a planar view for explaining another structure of the light irradiation apparatus shown in FIG. 11;

FIG. 17 is a cross-sectional view for explaining another structure of the light irradiation apparatus shown in FIG. 11;

FIG. 19 shows an optical path of the measurement light in the microplate and the light guiding member shown in FIG. 11.

DESCRIPTION OF EMBODIMENTS

Figure 1:
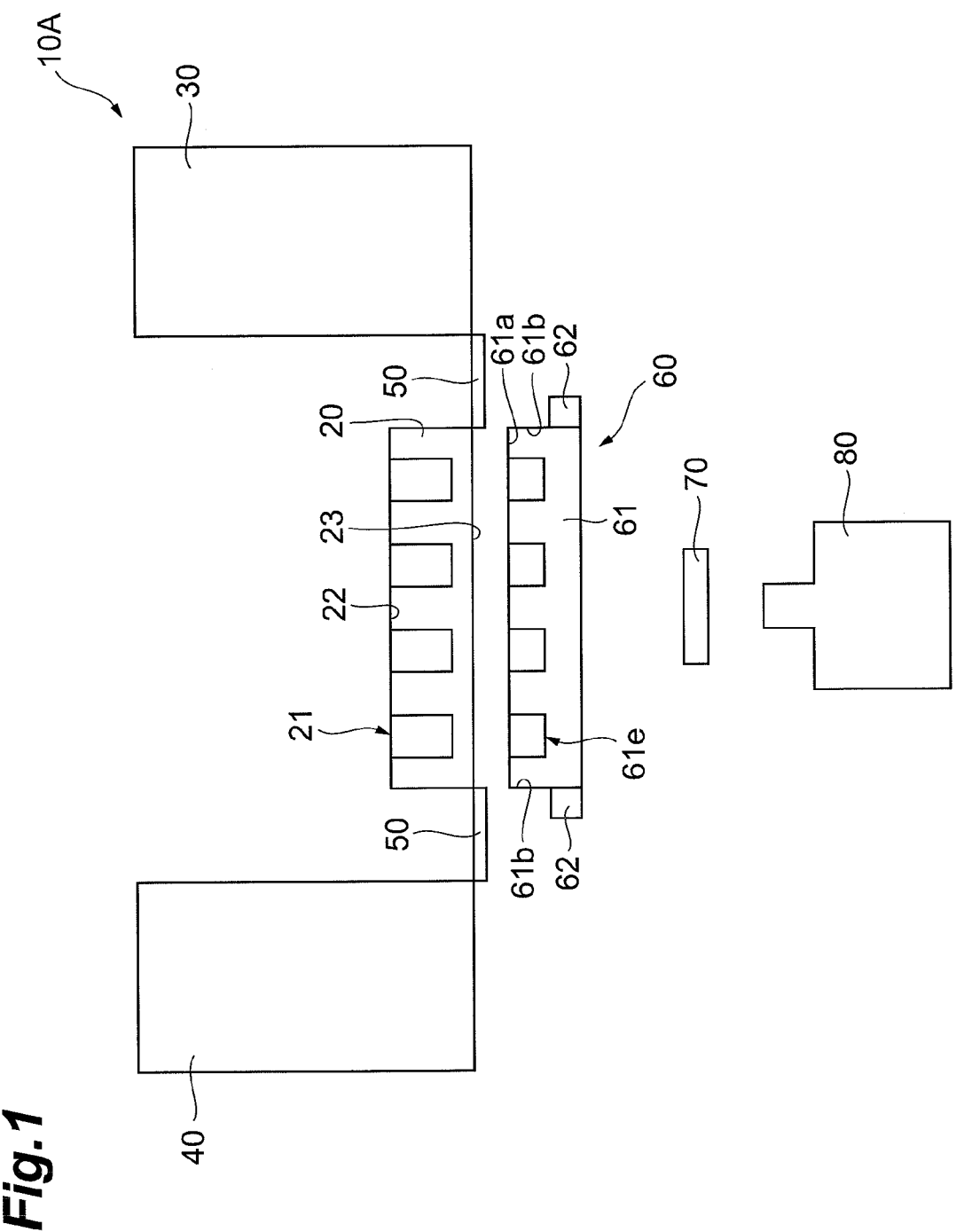
FIG. 1 shows a configuration of a first embodiment of a light measurement apparatus according to the present invention.
Figure 4:
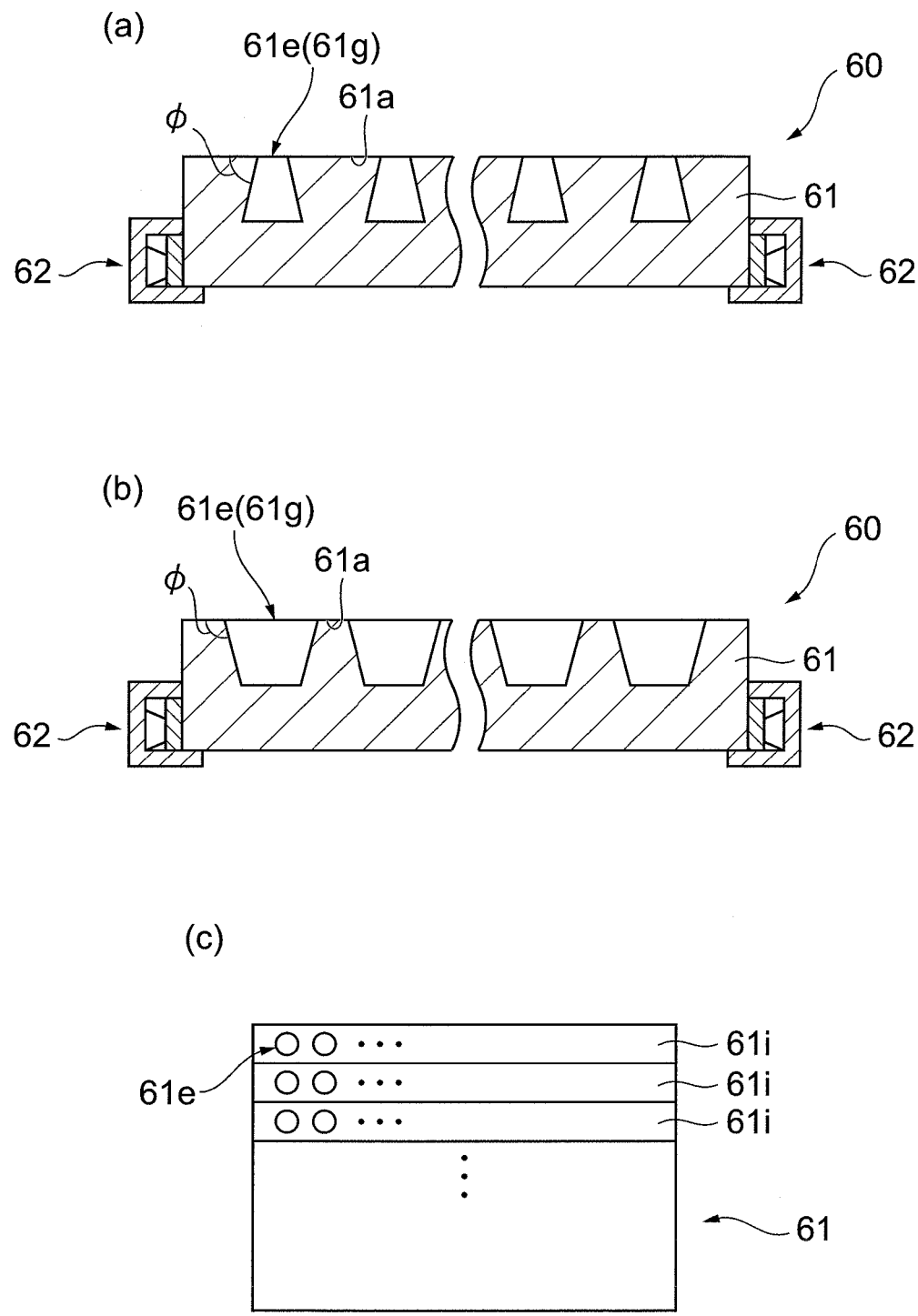
FIG. 4 is a view for explaining another structure of the light irradiation apparatus shown in FIG. 1.

In the following, embodiments of the light irradiation apparatus and the light measurement apparatus according to the present invention will be explained in detail below, with reference to FIGS. 1 to 19. In the description of the drawings, identical or corresponding components are designated by the same reference numerals, and overlapping description is omitted.

First Embodiment

FIG. 1 shows a configuration of the first embodiment of the light measurement apparatus according to the present invention. As shown in FIG. 1, the light measurement apparatus 10A comprises a microplate 20, microplate stockers 30 and 40, a transportation belt 50, a light irradiation apparatus 60, a pumping light cut filter 70, and a detector 80. In addition, the light irradiation apparatus 60 comprises a light guiding member 61 and a light source apparatus 62. The light measurement apparatus 10A detects light to be measured (simply referred to emitted light in the following, such as fluorescence emitted from an object to be measured), which has been emitted from an object to be measured by irradiating measurement light (pumping light) on the object to be measured held by the microplate 20.

FIG. 2 shows a structure of the microplate. In FIG. 2, the area (a) is a planar view of the microplate 20, and the area (b) is a cross-sectional view of the microplate 20 taken along line I-I in the area (a). As shown in the areas (a) and (b) of FIG. 2, the microplate 20 has a plurality of (e.g., 96) wells 21 on a main surface 22, each being a columnar depression. The wells 21 on the main surface 22 of the microplate 20 has openings arranged two-dimensionally, (eight columns×12 rows), for example. In addition, an object to be measured A such as cells, and solution B such as culture fluid, fluorescence indicator, evaluation compounds or the like are respectively injected into each of the wells 21. The object to be measured A is deposited on the bottom of each of the wells 21. Each of the wells 21 of the microplate 20 is not limited to a columnar depression. For example, each of the wells 21 of the microplate 20 may be a prism-shaped depression as shown in the area (c) of FIG. 2 (wells 21a).

Referring to FIG. 1 again, the microplate stocker 30 stores the microplate 20 to be measured. In addition, the microplate stocker 40 stores the measured microplate 20. The transportation belt 50 transports the microplate 20 to be measured from the microplate stocker 30 to a predetermined measurement position (position the microplate stocker can face the light irradiation apparatus 60). Furthermore, the transportation belt 50 transports the measured microplate 20 from the predetermined measurement position to the microplate stocker 40.

In the first embodiment, the light irradiation apparatus 60 includes the light guiding member 61 and the light source apparatus 62. The light guiding member 61 is made of silica glass, for example. The light source apparatus 62 emits measurement light into a side surface 61b of the light guiding member 61. The light irradiation apparatus 60 irradiates the measurement light on each of the wells 21 from a back surface 23 of the microplate 20. Here, the light measurement apparatus 10A according to the first embodiment has a mechanism (not shown) for moving the light irradiation apparatus 60 along a direction perpendicular to the back surface 23 (depth direction of the wells 21 of the microplate 20). The light irradiation apparatus 60 may be fixed at a position where the main surface 61a of the light guiding member 61 and the back surface 23 of the microplate 20 are separated with a predetermined interval (e.f., about 5 mm). In this case, the microplate 20 is transported to a predetermined measurement position without colliding with the light irradiation apparatus 60.

The pumping light cut filter 70 prevents transmission of the measurement light (pumping light), and transmits the light emitted from the object to be measured A. The detector 80 is provided on the back surface 23 of the microplate 20 to detect the emitted light from the object to be measured A. In addition, the detector 80 has an optical system (not shown) for forming an image with the emitted light which has been transmitted through the pumping light cut filter 70 and a light detection apparatus such as a two-dimensional CCD camera for capturing the formed image. The detector 80 may be provided on the main surface 22 of the microplate 20. In this case, the detector 80 may be, for example, a plurality of photomultipliers respectively arranged on each of the wells 21 of the microplate 20, or a two-dimensional image capturing apparatus which can capture images of the wells 21 of the microplate 20. When the photomultipliers are used as the detector 80, the emitted light from each of the wells 21 becomes detectable by moving the photomultipliers over the main surface 22 of the microplate 20.

Next, the light irradiation apparatus 60 will be described in detail. FIG. 3 shows the structure of the light irradiation apparatus 60. In FIG. 3, the area (a) is a cross-sectional view of the light irradiation apparatus 60 taken along line II-II in the area (b), and the area (b) is a planar view of the light irradiation apparatus 60. As shown in the areas (a) and (b) of FIG. 3, the light guiding member 61 of the light irradiation apparatus 60 has a main surface 61a, two side surfaces 61b which are generally perpendicular to the main surface 61a and opposing each other, two side surfaces 61c which are generally perpendicular to the main surface 61a and opposing each other, and a back surface opposing the main surface 61a. In addition, the light guiding member 61 has a plurality of depressions 61e two-dimensionally arranged on the main surface 61a as light emitting units which control the direction of emission of the measurement light to prevent the light from being perpendicularly incident on the back surface 23 of the microplate 20. Each of the depressions 61e is a columnar depression having an opening on the main surface 61a of the light guiding member 61 and includes a flat bottom 61f which is generally parallel to the light emitting surface 61a. The bottom 61f is mirror-finished.

The side surface 61b of the light guiding member 61 has the light source apparatus 62 provided thereon. The light source apparatus 62 includes a frame 62a, a plurality of LEDs 62b as light sources, and a filter 62c. The LEDs 62b are held by the frame 62a in a manner arranged along the side surface 61b of the light guiding member 61. The LEDs 62b emits directional measurement light toward the side surface 61b of the light guiding member 61 via the filter 62c. The filter 62c is a short-pass filter or a bandpass filter which transmits only the light having a particular wavelength band, and transmits, among the light emitted from the LED 62b, only the measurement light having a wavelength suitable for measurement. Accordingly, the light having a wavelength more suitable for measurement is guided into the light guiding member 61 as the measurement light by combining the LEDs 62b and the filter 62c. Therefore, according to the apparatus configuration described above, the precision of measurement can be raised.

Each depression 61e of the light guiding member 61 is not limited to a columnar depression and may be a prism-shaped depression 61g, as shown in the area (c) of FIG. 3. Furthermore, the cross-section of each depression (depression 61e and depression 61g) of the light guiding member 61 (corresponding to the cross-section taken along line II-II in the area (b) of FIG. 3) may be a trapezoid-shaped depression as shown in the areas (a) and (b) of FIG. 4. In this case, it is preferred that the angle φ formed by the side surface of each depression (depression 61e and depression 61g) and the main surface 61a of the light guiding member 61 is an acute angle. However, the angle φ may be an obtuse angle about 90 to 120 degrees. In addition, the light guiding member 61 may be formed by arranging a plurality of prism-shaped optical fibers 61i each having the depressions 61e as shown in the area (c) of FIG. 4. In the light guiding member 61, as thus described, the bottom surface of each well 21 and the opening of each depression 61e can be arranged so as to face each other, as shown in FIG. 1. It is preferable that the depth of each depression (depression 61e and depression 61g) of the light guiding member 61 is about 2 mm.

Figure 5:
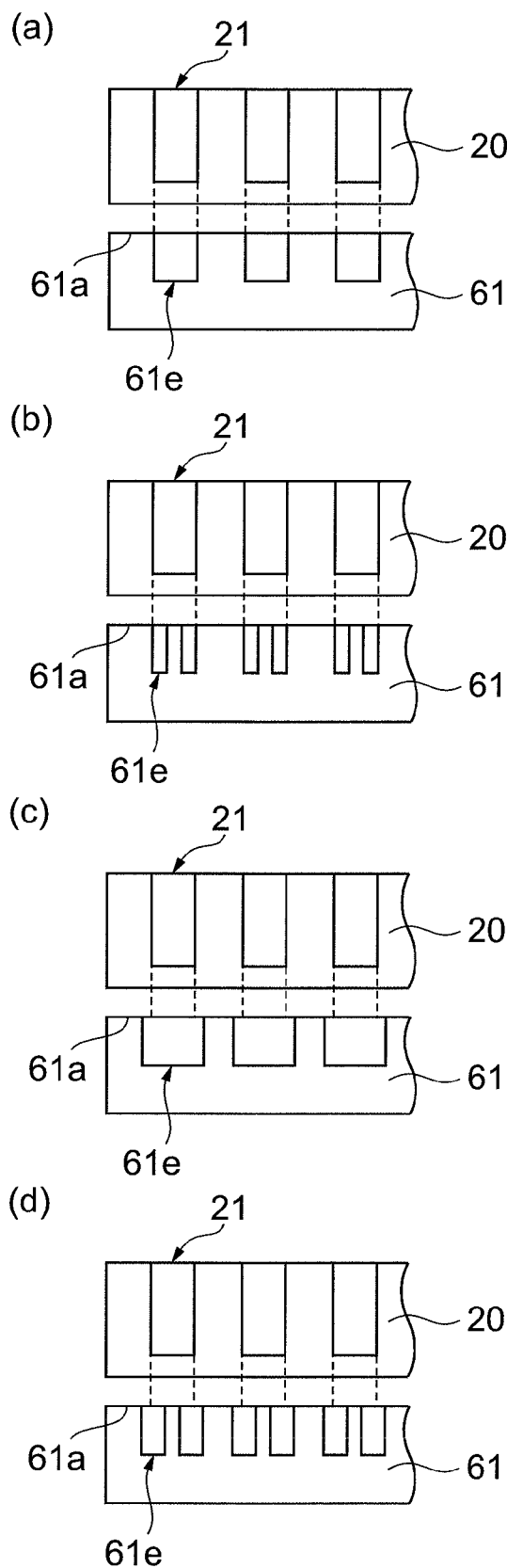
FIG. 5 is a view for explaining a positional relation between wells of the microplate and depressions of a light guiding member shown in FIG. 1.

FIG. 5 is a schematic explanatory view of a variation of an arrangement pattern of the depressions 61e corresponding to the wells 21. Typically, it is preferred that each depression 61e is arranged in a manner corresponding to each of the wells 21 on a one-to-one basis, as shown in the area (a) of FIG. 5. However, the depressions 61e may be arranged in a manner corresponding to one of the wells 21, as shown in the area (b) of FIG. 5. In addition, each depression 61e may be arranged in a manner corresponding to each of the wells 21 on a one-to-one basis and having a wider width than each of the wells 21, as shown in the area (c) of FIG. 5. Furthermore, each depression 61e may be arranged so that the depressions 61e correspond to one of the wells 21, as shown in the area (d) of FIG. 5, and that a part of each depression 61e does not overlap the well 21 (and the remaining part of each depression 61e overlap the well 21), seen from above the main surface 61a.

Two types of LEDs which emit light having mutually different wavelengths can be used as the light source of the light source apparatus 62. In this case, as shown in the area (a) of FIG. 6, a plurality of LEDs 62b are arranged along the side surface 61b of the light guiding member 61, whereas a plurality of LEDs 62d (each being an LED which emits light having a different wavelength from the LEDs 62b) are arranged along another side surface 61c of the light guiding member 61. According to such a configuration, the light source apparatus 62 can supply measurement light having two mutually different wavelengths to the light guiding member 61. The filter 62c is arranged between the LEDs 62b and the light guiding member 61, whereas another filter 62e (a short-pass filter or a bandpass filter which transmits light having a different wavelength from the filter 62c) is arranged between the LEDs 62d and the light guiding member 61. Therefore, the filter 62e can transmit, among the light emitted from the LEDs 62d, only the measurement light having a wavelength suitable for measurement. Additionally, as shown in the area (b) of FIG. 6, the LEDs 62b and the LEDs 62d may be alternately arranged along the side surface 61b and the side surfaces 61c of the light guiding member 61. In this occasion, the filter 62c and the filter 62e are alternately arranged between the LEDs 62b, 62d and the light guiding member 61.

The light source of the light source apparatus 62 is not limited to LEDs. For example, a white light source such as a xenon lamp 62f can be used as the light source of the light source apparatus 62, as shown in the area (a) of FIG. 7. In this case, the xenon lamp 62f emits directional measurement light having a predetermined wavelength from the side surface 61b of the light guiding member 61 toward the light guiding member 61, via a wavelength switching apparatus 62g and an optical fiber 62h. Accordingly, light having a wavelength that cannot be realized by LEDs can be used as the measurement light. In this occasion, the xenon lamp 62f itself as the light source need not be arranged on the side surface 61b of the light guiding member 61, as shown in the area (a) of FIG. 7. In addition, using a given light source 62k which emits non-directional light as the light source of the light source apparatus 62, a collimator lens 62n may be provided between the light source 62k and a filter 62m, as shown in the area (b) of FIG. 7. The collimator lens 62n may be provided on the side surface 61b of the light guiding member 61 integrally with the light guiding member 61, as shown in the area (c) of FIG. 7. The filter 62m transmits only the measurement light having a wavelength suitable for measurement among the light emitted from the light source 62k.

Figure 8:
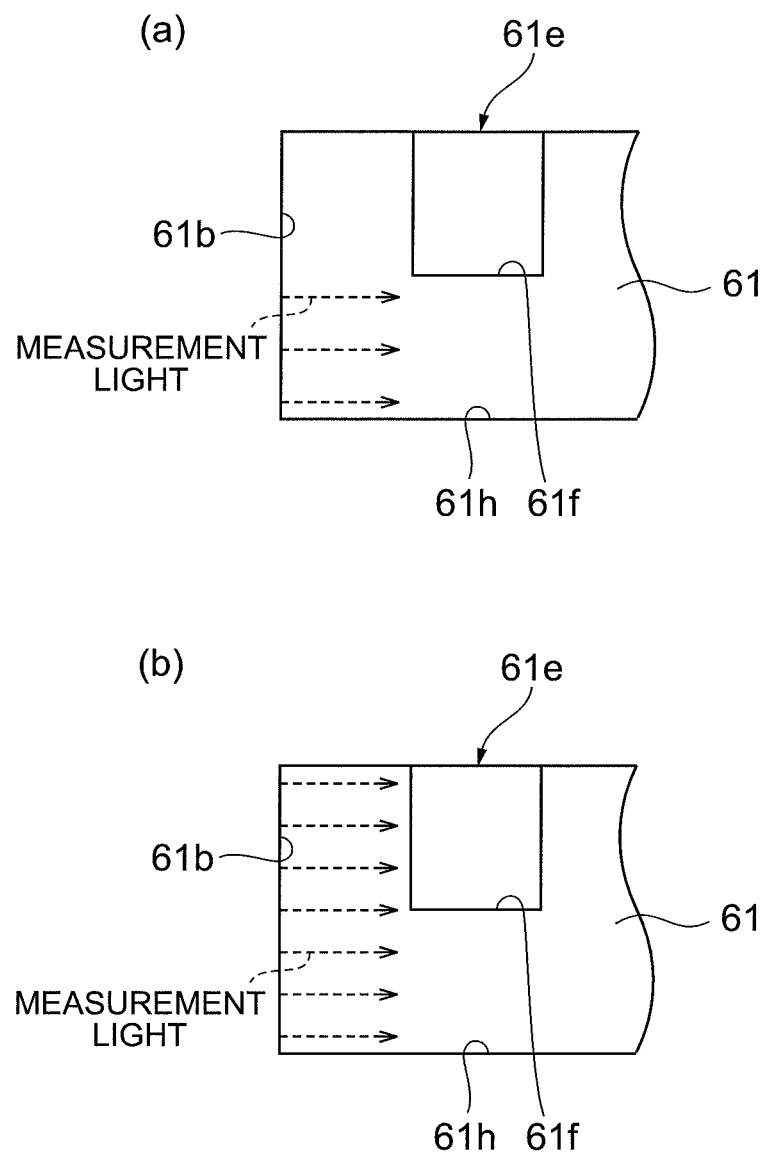
FIG. 8 is a view for explaining how the measurement light is incident in the light irradiation apparatus shown in FIG. 1.

FIG. 8 is a view for explaining how the measurement light guided into the light guiding member 61 is incident. As shown in the area (a) of FIG. 8, it is preferred that the measurement light is guided into the light guiding member 61 from a part corresponding to a region between the back surface 61f of each depression 61e and a bottom surface 61h of the light guiding member 61 (back surface of the light guiding member 61) of the side surfaces 61b. However, the measurement light may be guided into the light guiding member 61 from the entire side surface 61b, as shown in the area (b) of FIG. 8.

Figure 9:
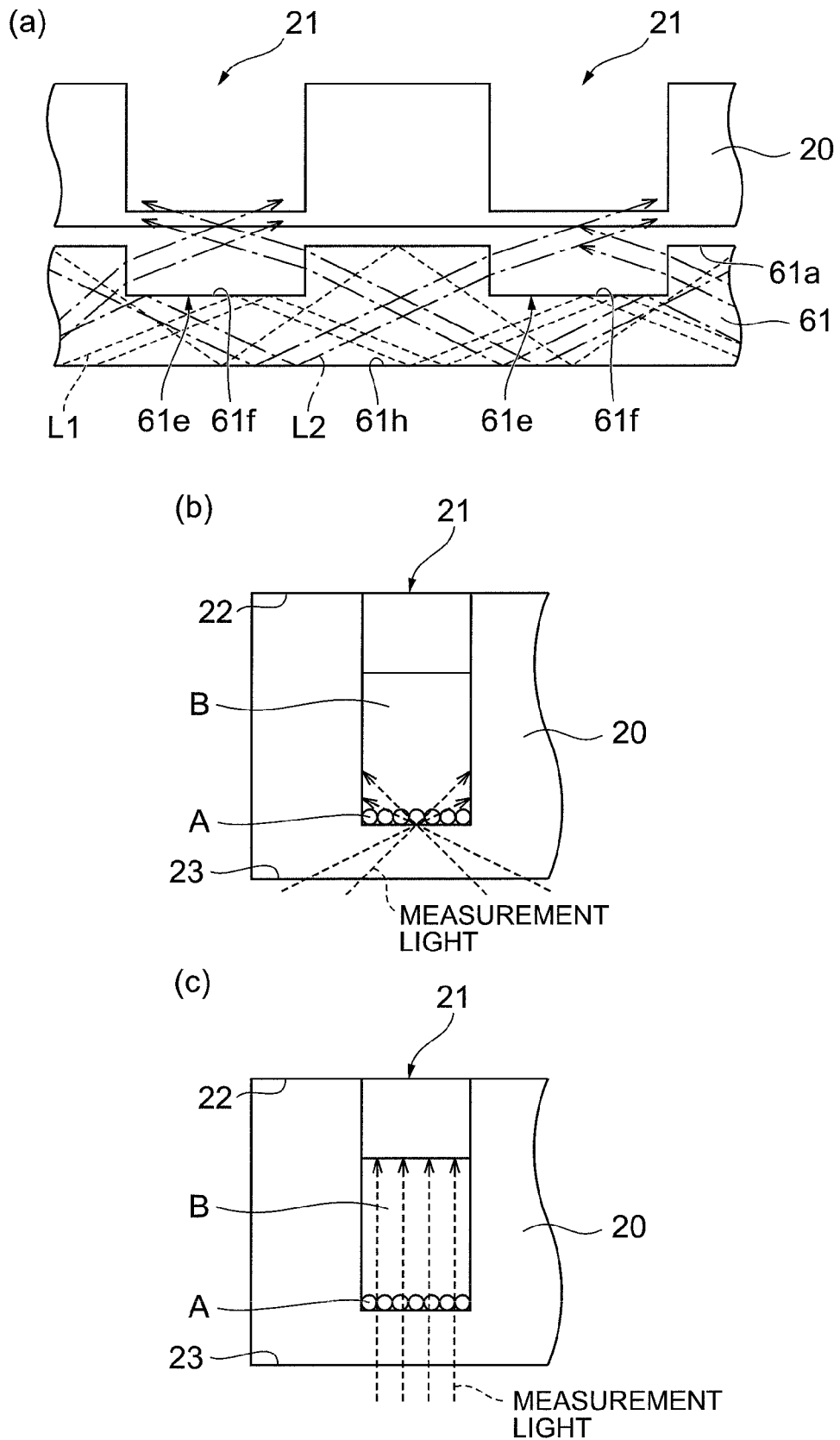
FIG. 9 is a view for explaining an optical path of the measurement light in the microplate and the light guiding member shown in FIG. 1.

As thus described, with the light irradiation apparatus 60 of the light measurement apparatus 10A according to the first embodiment, directional measurement light is incident from the side surface 61b of the light guiding member 61 on the light guiding member 61 having the depressions 61e formed on the main surface 61a. As is shown in the area (a) of FIG. 9, a part of the measurement light incident on the light guiding member 61 travels along the optical path shown by the dashed line L1, and is totally reflected at the bottom surface 61f of each depression 61e, and the back surface 61h and the main surface 61a of the light guiding member 61. Therefore, incidence of the component of the measurement light traveling along the depth direction of each well 21 into each depression 61e can be effectively suppressed. In addition, a part of the measurement light incident in the light guiding member 61 travels along the optical path shown by the long dashed short dashed line L2 in the area (a) of FIG. 9, and reaches from the side surface of each depression 61e inside each corresponding depression 61e. Such a measurement light component is refracted due to the refractive index difference the light guiding member 61 and air inside each depression 61e toward a direction parallel to the light emitting surface 61a, and irradiated on each of the wells 21. Accordingly, the direction of travel of the measurement light incident on the wells 21 is inclined against the depth direction of the wells 21. Therefore, as shown in the area (b) of FIG. 9, the measurement light irradiated on the solution B is relatively reduced. Hence, background light noise from each of the wells 21 caused by irradiation of the measurement light on solution B is effectively reduced. In contrast, the area (c) of FIG. 9 illustrates the optical path of measurement light when the measurement light traveling along the depth direction of the well (measurement light perpendicularly incident on each of the wells 21) is irradiated on each of the wells 21 by a conventional method. According to the conventional method, as shown in the area (c) of FIG. 9, a large amount of measurement light is irradiated on the solution B, as well as the object to be measured A. Therefore, the conventional method causes background light noise from each of the wells 21 to be relatively larger than the light measurement apparatus 10A according to the first embodiment to which the light irradiation apparatus 60 is applied.

Figure 10:
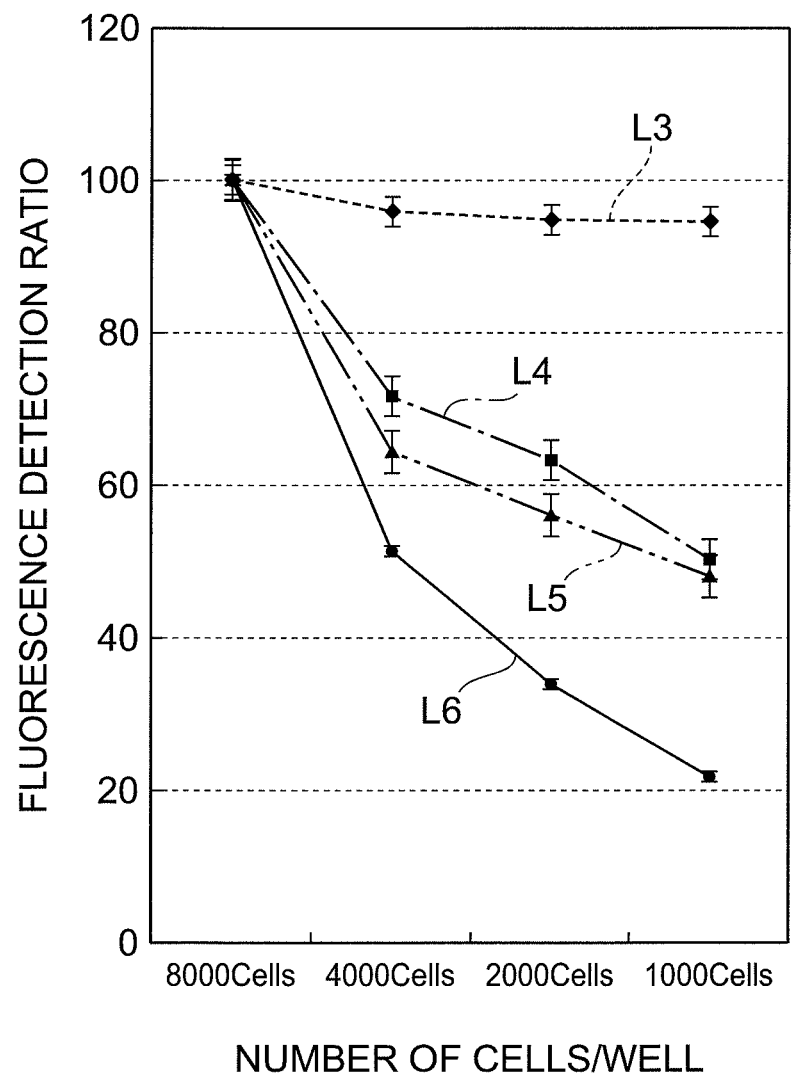
FIG. 10 is a graph showing the measurement result of light emitted from the object to be measured held by the microplate shown in FIG. 1 and the solution (light to be measured such as fluorescence)

FIG. 10 is a graph showing the measurement result of fluorescence which is the emitted light (light to be measured) from the object to be measured A or the like. In the graph shown in FIG. 10, the horizontal axis expresses the number of cells (object to be measured A) injected into each of the wells 21, and the vertical axis expresses the fluorescence detection ratio. The cells injected into each of the wells 21 are dyed with fluorescent dyeing pigment. The measurement result expressed by the dashed line L3 is the fluorescence measurement result of a case (conventional method) where the measurement light is perpendicularly incident (incident in parallel to the depth direction of the well) on the wells 21 after the cells and the fluorescence solution (solution B: FITC) are injected into each of the wells 21 of the microplate 20. The measurement result expressed by the long dashed short dashed line L4 is the fluorescence measurement result of irradiating the measurement light on each of the wells 21 using the light irradiation apparatus 60 after injecting the cells and the fluorescence solution into each of the wells 21 of the microplate 20. In the measurement expressed by the long dashed short dashed line L4, the depth of each depression 61e of the light guiding member 60 is 4 mm. The measurement result expressed by long dashed double-short dashed line L5 is the fluorescence measurement result of irradiating the measurement light on each of the wells 21 using the light irradiation apparatus 60, after injecting the cells and the fluorescence solution into each of the wells 21 of the microplate 20. In the measurement of long dashed double-short dashed line L5, the depth of each depression 61e of the light guiding member 61 of the light irradiation apparatus 60 is 1 mm. The measurement result expressed by the solid line L6 is the fluorescence measurement result of irradiating the measurement light on each of the wells 21, after injecting (washing out) only the cells into each of the wells 21 of the microplate 20. In the graph of FIG. 10, therefore, the closer to the result expressed by the solid line L6 the more background light noise is reduced from the fluorescence solution. According to the measurement result shown in the graph of FIG. 10, it can be seen that the measurement result of irradiating light using the light irradiation apparatus 6 expressed by the long dashed short dashed line L4 and the long dashed double-short dashed line L5 is closer to the measurement result expressed by the solid line L6 compared with the measurement result by the conventional light irradiation method expressed by the dashed line L3. Therefore, it can be seen that background light noise from each of the wells 21 in the microplate 20 has been effectively reduced by the light irradiation apparatus 60 applied to light measurement apparatus 10A according to the first embodiment.

Second Embodiment

Figure 11:
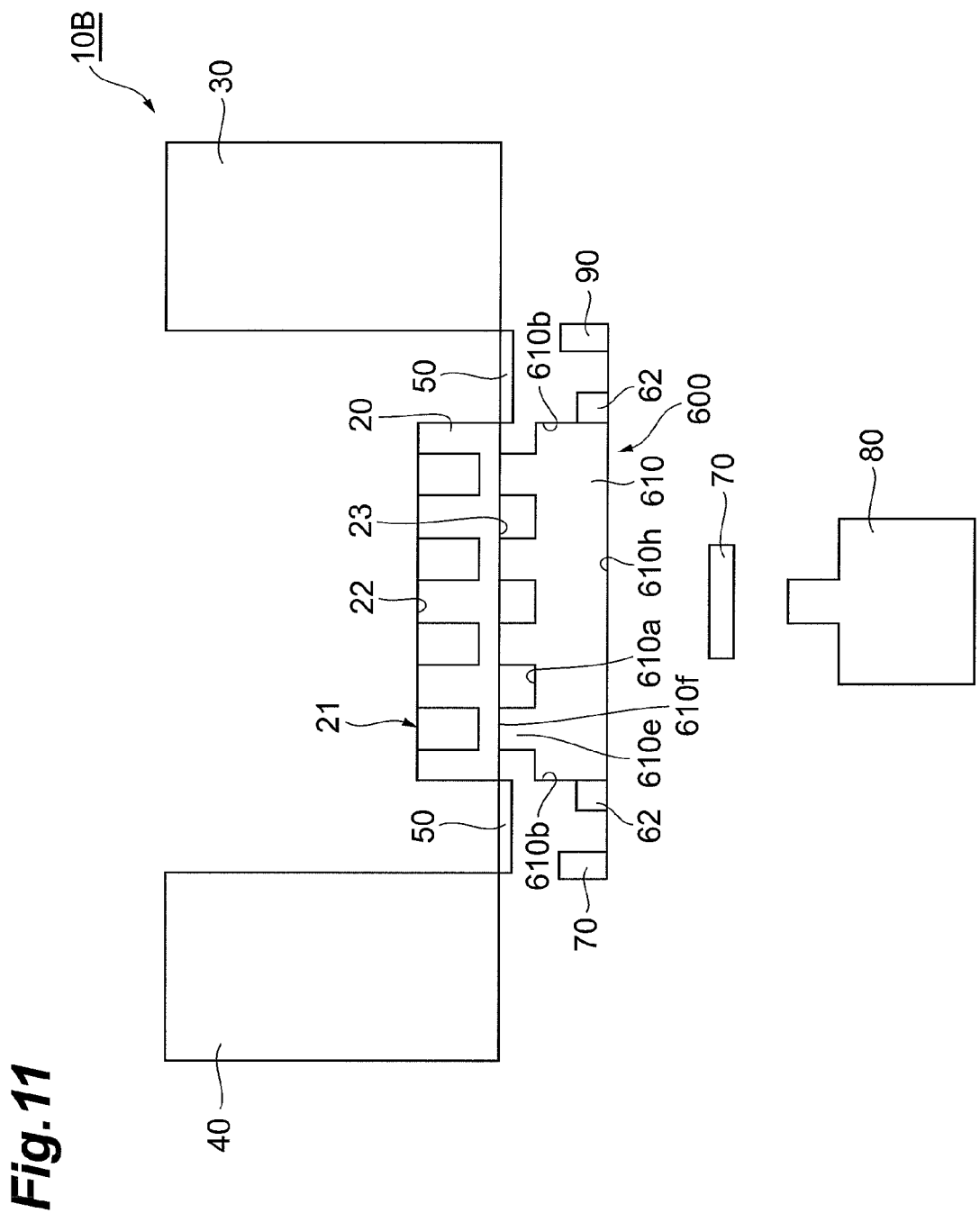
FIG. 11 is a view for explaining a configuration of a second embodiment of the light measurement apparatus according to the present invention.

Next, FIG. 11 shows a configuration of a second embodiment of the light measurement apparatus according to the present invention. As shown in FIG. 11, the light measurement apparatus 10B comprises the microplate 20, the microplate stockers 30 and 40, the transportation belt 50, a light irradiation apparatus 600, a moving unit 90, the pumping light cut filter 70, and the detector 80. In addition, the light irradiation apparatus 600 includes a light guiding member 610 and the light source apparatus 62. The light measurement apparatus 10B detects the emitted light from the object to be measured (light to be measured such as fluorescence) by irradiating the measurement light (pumping light) on the object to be measured held by the microplate 20.

Figure 12:
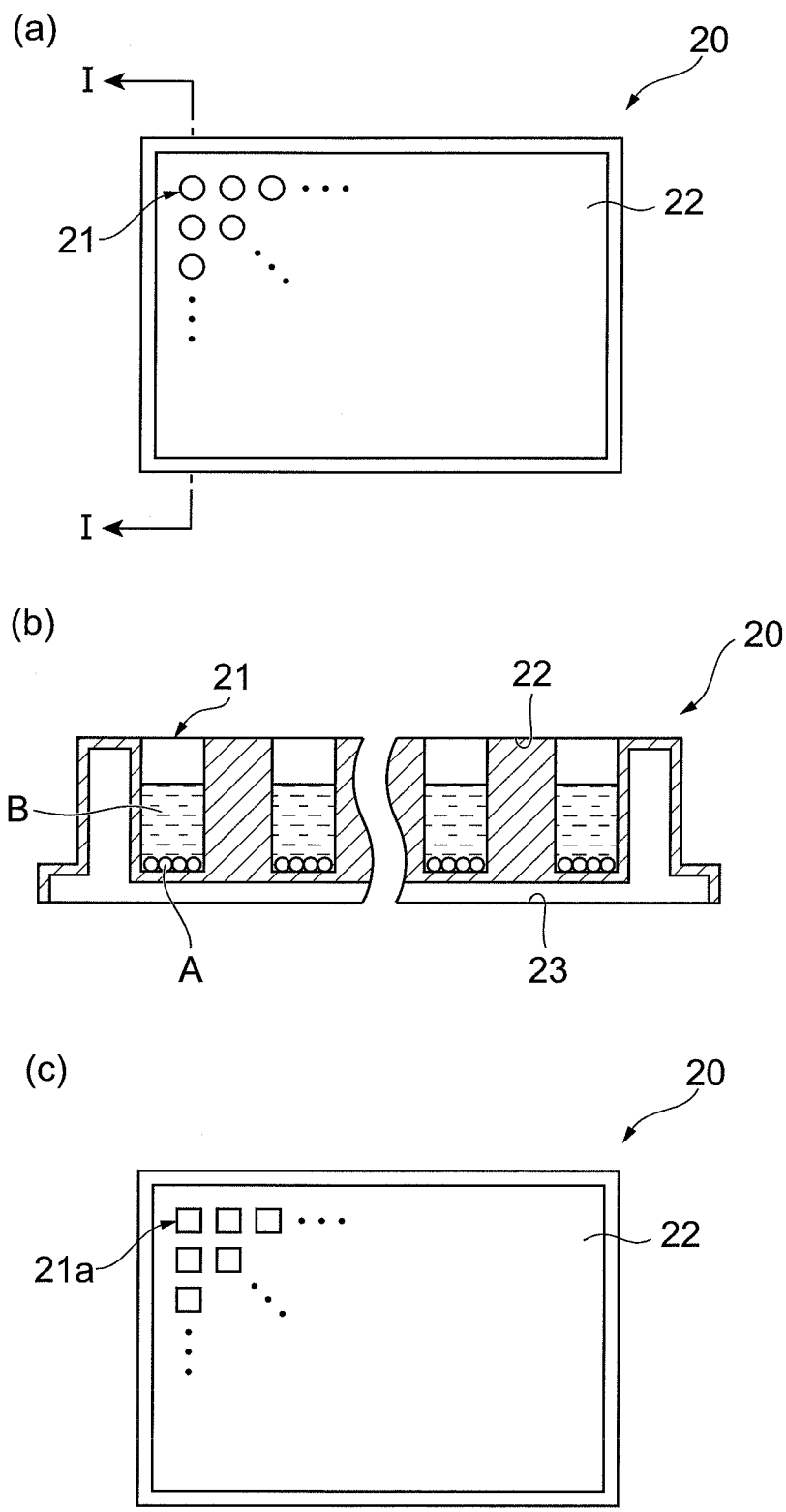
FIG. 12 is a view for explaining the structure of the microplate shown in FIG. 11.

FIG. 12 shows the structure of the microplate 20. In FIG. 12, the area (a) is a planar view of the microplate 20, and the area (b) is a cross-sectional view of the microplate 20 taken along line I-I in the area (a). The microplate 20 has a plurality of (e.g., 96) wells 21 each being a columnar depression as shown in the areas (a) and (b) of FIG. 12. The wells 21 on the main surface 22 of the microplate 20 has openings which are arranged two-dimensionally, (eight columns×12 rows), for example. In addition, the object to be measured A such as cells, and the solution B such as culture fluid, fluorescence indicator, evaluation compounds or the like are respectively injected into the wells 21. The object to be measured A is deposited on the bottom of the wells 21. The wells 21 of the microplate 20 are not limited to columnar depressions. For example, the wells of the microplate 20 may be prism-shaped depressions as shown in the area (c) of FIG. 12 (wells 21a).

Referring to FIG. 11 again, the microplate stocker 30 stores the microplate 20 to be measured. In addition, the microplate stockers 40 stores the measured microplate 20. The transportation belt 50 transports the microplate 20 to be measured from the microplate stocker 30 to a predetermined measurement position (position where the microplate can face the light irradiation apparatus 600). Furthermore, the transportation belt 50 transports the measured microplate 20 from the predetermined measurement position to the microplate stocker 40.

In the second embodiment, the light irradiation apparatus 600 includes the light guiding member 610 and the light source apparatus 62. The light guiding member 610 is made of silica glass, for example. The light source apparatus 62 emits measurement light into a side surface 610b of the light guiding member 610. The light irradiation apparatus 600 irradiates the measurement light on each of the wells 21 from a back surface 23 of the microplate 20. The moving unit 90 includes a motor or the like, and moves the light irradiation apparatus 600 along a direction perpendicular to the back surface 23 of the microplate 20 (the depth direction of the well of the microplate 20).

The pumping light cut filter 70 prevents transmission of the measurement light, and transmits the emitted light (fluorescence) from the object to be measured A. The detector 80 is provided on the back surface 23 of the microplate 20 to detect the emitted light from the object to be measured A. In addition, the detector 80 has an optical system (not shown) for forming an image with the emitted light which has been transmitted through the pumping light cut filter 70 and a light detection apparatus such as a two-dimensional CCD camera for capturing the formed image. The detector 80 may be provided on the main surface 22 of the microplate 20. In this case, the detector 80 may be, for example, a plurality of photomultipliers respectively arranged on each of the wells 21 of the microplate 20, or a two-dimensional image capturing apparatus which can capture image of the wells 21 of the microplate 20. When the photomultipliers are used as the detector 80, the emitted light from each of the wells 21 becomes detectable by moving the photomultipliers over the main surface 22 of the microplate 20.

Figure 13:
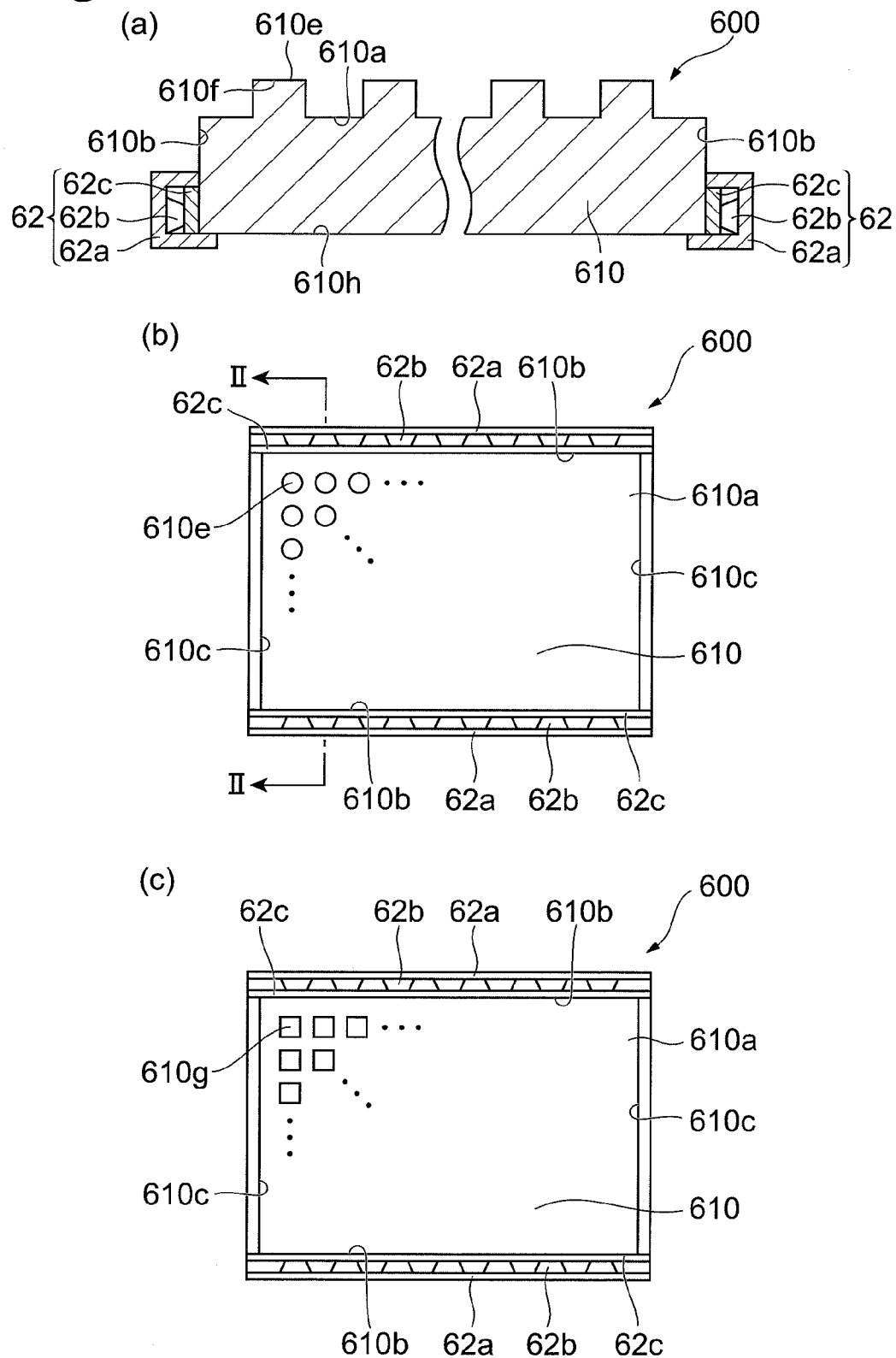
FIG. 13 is a view for explaining the structure of the light irradiation apparatus shown in FIG. 11.

Next, the light irradiation apparatus 600 will be described in detail. In FIG. 13, the area (a) is a cross-sectional view of the light irradiation apparatus 600 taken along line II-II the area (b), and the area (b) is a planar view of the light irradiation apparatus 600. As shown in the area (a) and (b) of FIG. 13, the light guiding member 610 of the light irradiation apparatus 600 has a main surface 610a, two side surfaces 610b which are generally perpendicular to the main surface 610a and opposing each other, two others side surfaces 610c which are generally perpendicular to the main surface 610a and opposing each other, and a back surface 610h opposing the main surface 610a. In addition, the light guiding member 610 has a plurality of protrusions 610e two-dimensionally arranged on the main surface 610a as light emitting units and integrally provided on the main body (region surrounded by the main surface 610a, the side surface 610b, the side surface 610c, and the back surface 610h) of the light guiding member 610. Each of the protrusions 610e has generally the same shape. Each of the protrusions 610e is a columnar projection having a flat upper surface 610f which is generally parallel to the main surface 610a. The main surface 610a and the back surface 610h are mirror-finished The side surface 610b of the light guiding member 610 has the light source apparatus 62 provided thereon. The light source apparatus 62 includes the frame 62a, the LED s62b as the light source, and the filter 62c. The LEDs 62b are held by the frame 62a in a manner arranged along the side surface 610b of the light guiding member 610. The LEDs 62b emit directional measurement light from the side surface 610b of the light guiding member 610 toward the light guiding member 610 via the filter 62c. The filter 62c is a short-pass filter or a bandpass filter which transmits only the light having a particular wavelength band, and transmits, among the light emitted from the each LED 62b, only the measurement light having a wavelength suitable for measurement. Accordingly, the light having a wavelength more suitable for measurement is guided into the light guiding member 610 by combining the LEDs 62b and the filter 62c. Therefore, according to the apparatus configuration described above, the precision of measurement can be raised. The light guiding member 610 described above may be provided so that the upper surface 610f of each protrusion 610e contacts the back surface 23 of the microplate 20, as shown in FIG. 11. In addition, the light guiding member 610 may be provided so that the upper surface 610f of each protrusion 610e faces the bottom surface of wells 21 of the microplate 20.

Each protrusion 610e of the light guiding member 610 is not limited to a columnar projection and may be a protrusion 610g of a prism-shaped projection, as shown in the area (c) of FIG. 13. Furthermore, the protrusion 610e (protrusion 610g) may be a cylindrical (or square-cylindrical) projection, inside of which is hollowed. Additionally, as shown in the area (a) of FIG. 14, each protrusion 610e may be formed by a different material (e.g., silicone) from the main body of the light guiding member 610. It is preferred that the material of each protrusion 610e has a higher refractive index than the light guiding member 610. In this case, since it becomes easier for the measurement light to transmit from the light guiding member 610 to each protrusion 610e, a still larger amount of measurement light is emitted from the upper surface 610f of each protrusion 610e toward the back surface of the microplate 20. Additionally, as shown in the area (b) of FIG. 14, the region between the protrusions 610e may be filled with a filling member 610j. It is preferred that the filling member 610j has a lower refractive index than each protrusion 610e. Accordingly, leakage of the measurement light incident on each protrusion 610e, i.e. leakage of the measurement light from the side surface of each protrusion 610e is effectively suppressed. Furthermore, it is preferred that the filling member 610j has a lower refractive index than the light guiding member 610. Accordingly, incidence of the measurement light from the light guiding member 610 to filling member 610j is effectively suppressed. Additionally, as shown in the area (c) of FIG. 14, the light guiding member 610 may be formed by arranging a plurality of prisms-shaped optical fiber 610i each having a plurality of protrusions 610e provided thereon.

FIG. 15 is a schematic explanatory view of a variation of an arrangement pattern of the protrusions 610e corresponding to the wells 21. It is preferred that each protrusion 610e is arranged in a manner corresponding to each of the wells 21 on a one-to-one basis, as shown in the area (a) of FIG. 15. However, the protrusions 610e may be arranged in a manner corresponding one of the wells 21, as shown in the area (b) of FIG. 15. Furthermore, each protrusion 610e may be arranged so that each protrusion 610e does not overlap the well 21, seen from above the main surface 610a, as shown in the area (c) of FIG. 15 is not piled up.

Two types of LEDs which emit light having mutually different wavelengths can be used as the light source of the light source apparatus 62. In this case, as shown in the area (a) of FIG. 16, the LEDs 62b are arranged along the side surface 610b of the light guiding member 610, whereas the LEDs 62d (each being an LED which emits light having a different wavelength from the LEDs 62b) are provided along another side surface 610c of the light guiding member 610. According to such a configuration, the light source apparatus 62 can emit measurement light having two mutually different wavelengths to the light guiding member 610. The filter 62c is arranged between the LEDs 62b and the light guiding member 610, whereas another filter 62e (a short-pass filter or a bandpass filter which transmits light having a different wavelength from the filter 62c) is arranged between the LEDs 62d and the light guiding member 610. The filter 62e transmits, among the light emitted from the LEDs 62d, only the measurement light having a wavelength suitable for measurement. Additionally, as shown in the area (b) of FIG. 16, the LEDs 62b and the LEDs 62d may be alternately arranged along the side surface 610b and the side surface 610c of the light guiding member 610. In this occasion, the filter 62c and filter 62e are alternately arranged between the LEDs 62b, 62d and the light guiding member 610.

The light source of the light source apparatus 62 is not limited to LEDs. For example, a white light source such as xenon lamp 62f can be used the light source of the light source apparatus 62, as shown in the area (a) of FIG. 17. In this case, the xenon lamp 62f emits directional measurement light having a predetermined wavelength toward the side surface 610b of the light guiding member 610, via the wavelength switching apparatus 62g and the optical fiber 62h. Accordingly, light having a wavelength that cannot be realized by LEDs can be used as the measurement light. In this occasion, the xenon lamp 62f itself as the light source need not be arranged on the side surface 610b of the light guiding member 610, as shown in the area (a) of FIG. 17. In addition, using the given light source 62k which emits nondirectional light as the light source of the light source apparatus 62, the collimator lens 62n may be provided between the light source 62k and the filter 62m, as shown in the area (b) of FIG. 17. The collimator lens 62n may be provided on the side surface 610b of the light guiding member 610 integrally with the light guiding member 610, as shown in the area (c) of FIG. 17. The filter 62m transmits only the measurement light having a wavelength suitable for measurement among the light emitted from the light source 62k.

Figure 18:
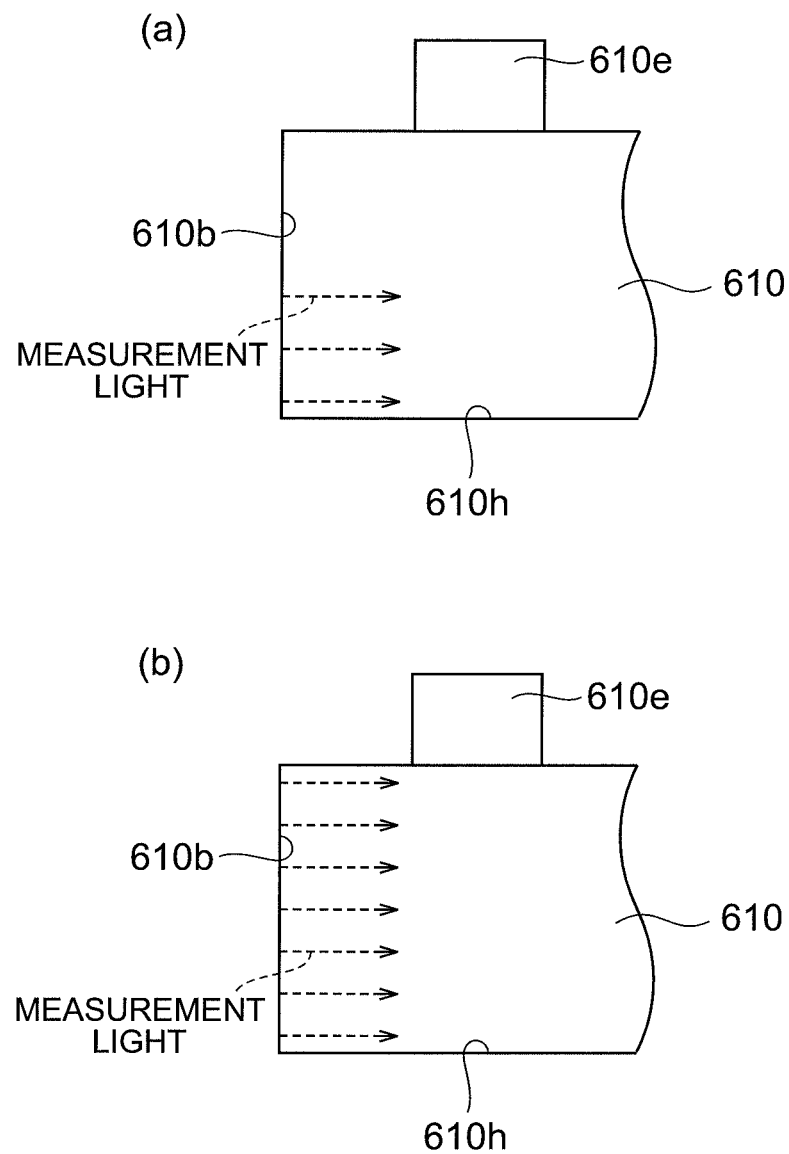
FIG. 18 is a view for explaining how the measurement light is incident in the light irradiation apparatus shown in FIG. 11.

FIG. 18 is a view for explaining how the measurement light is incident in the light guiding member 610. As shown in the area (a) of FIG. 18, the measurement light may be guided into the light guiding member 610 from a part of the side surface 610b (e.g., a part of the bottom surface 610h). Additionally, as shown in the area (b) of FIG. 18, the measurement light may be guided into the light guiding member 610 from the entire side surface 610b.

As thus described, with the light irradiation apparatus 600 applied to the light measurement apparatus 10B according to the second embodiment, directional measurement light is incident from the side surface 610b of the light guiding member 610 on the light guiding member 610 having the protrusions 610e formed on the main surface 610a. A part of the measurement light incident on the light guiding member 610 travels along the optical path shown by the dashed line L1 in the area (a) of FIG. 19, and is totally reflected at the back surface 610h and the main surface 610a of the light guiding member 610. In addition, a part of the measurement light incident on the light guiding member 610 travels along the optical path shown by the long dashed short dashed line L2 in the area (a) of FIG. 19 and, after having been reflected at the main surface 610a of the light guiding member 610 and back surface 610h, reaches each protrusion 610e. Such a measurement light component is emitted from the upper surface 610f of each protrusion 610e, and irradiated on the corresponding wells 21 via the back surface 23 of the microplate 20 contacting each protrusion 610e. Accordingly, the measurement light emitted from the upper surface 610f of each protrusion 610e is irradiated on the wells 21 in a manner inclined against the depth direction of the wells 21. Therefore, as shown in the area (b) of FIG. 19, the measurement light irradiated on the solution B is relatively reduced. Hence, background light noise from each of the wells 21 caused by irradiation of the measurement light on the solution B is effectively reduced. In addition, since the main surface 610a and the back surface 610h of the light guiding member 610 is mirror-finished, a part of the measurement light incident on the light guiding member 610 from the side surface 610b of the light guiding member 610 is totally reflected at the main surface 610a and the back surface 610h of the light guiding member 610. Accordingly, leakage of the measurement light incident on the light guiding member 610 from the light guiding member 610 is effectively suppressed. In contrast, the area (c) of FIG. 19 illustrates the optical path of the measurement light when the measurement light is perpendicularly incident (incident along the depth direction of the well) on each of the wells 21 by a conventional method. According to the conventional method, as shown in the area (c) of FIG. 19, a large amount of measurement light is irradiated on the solution B, as well as the object to be measured A. Therefore, the conventional method causes background light noise from each of the wells 21 to be larger than the light measurement apparatus 10B according to the second embodiment to which the light irradiation apparatus 600 is applied.

REFERENCE SIGNS LIST 10A, 10B . . . light measurement apparatus; 20 . . . microplate; 21, 21a . . . well; 22, 61a, 610a . . . main surface; 23, 61h, 610h . . . back surface; 30, 40 . . . microplate stocker; 50 . . . transportation belt; 60, 600 . . . light irradiation apparatus; 61, 610 . . . light guiding member; 61b, 61c, 610b, 610c . . . side surface; 61e, 61g . . . depression; 610e, 610g . . . protrusion; 61f . . . bottom surface; 610f . . . upper surface; 610j . . . filling member; 62 . . . light source apparatus; 62a . . . frame; 62b, 62d . . . LED; 62c, 62e, 62m . . . filter; 62f . . . xenon lamp; 62g . . . wavelength switching apparatus; 61i, 610i, 62h . . . optical fiber; 62k . . . light source; 62n . . . collimator lens; 70 . . . pumping light cut filter; 80 . . . detector; and 90 . . . moving unit.

The invention claimed is:

1. A light measurement apparatus, comprising:
a light irradiation apparatus for irradiating a microplate having a main surface on which plural wells each accommodating, an object to be measured are two-dimensionally arranged and a back surface opposing the main surface, with measurement light from the back surface side of the microplate; and
a detector detecting light emitted from the object to be measured in response to the irradiation of the measurement light,
wherein the light irradiation apparatus comprises:
a light guiding member having a main surface, a back surface opposing the main surface, a side surface which intersects at least the back surface, and plural depressions in the main surface that act as light-emitting portions irradiating the object to be measured with the measurement light; and
a light source outputting the measurement light to be introduced within the light guiding member through the side surface thereof,
wherein the plural light-emitting portions are located between the main surface and the back surface of the light guiding member, and
wherein the detector is arranged so that the back surface of the light guiding member is located between the detector and the plural light-emitting portions.

2. The light measurement apparatus according to claim 1, further comprising:
microplate having a main surface on which plural wells each accommodating an object to be measured are two-dimensionally arranged and a back surface opposing the main surface, the microplate being arranged so as to directly face the main surface of the light guiding member of the light irradiation apparatus.

3. The light measurement apparatus according to claim 1, wherein each of plural light emitting portions includes one or more depressions each extending from the main surface toward the back surface of the light guiding member and having an opening on the main surface, and
wherein the measurement light, inputted into the light guiding member from the side surface thereof, is refracted and reflected at the side surface of each of the depressions, and then outputted from the opening of each of the depressions.

4. The light measurement apparatus according to claim 3, wherein each of the depressions is a columnar depression.

5. The light measurement apparatus according to claim 4, wherein each of the depressions has a flat bottom surface.

6. The light measurement apparatus according to claim 5, wherein the bottom surface of each of the depressions is mirror-finished.

7. The light measurement apparatus according to claim 3, wherein each of the depressions has a flat bottom surface.

8. The light measurement apparatus according to claim 7, wherein the bottom surface of each of the depressions is mirror-finished.

9. The light measurement apparatus according to claim 3, further comprising:
a microplate having a main surface on which plural wells each accommodating an object to be measured are two-dimensionally arranged and a back surface opposing the main surface, the microplate being arranged so as to directly face openings of plural depressions arranged on the main surface of the light guiding member in the light irradiation apparatus.

10. The light measurement apparatus according to claim 1, wherein each of the plural light emitting portions is located within the light guiding member while being apart from the side surface thereof.

11. A light irradiation apparatus for irradiating an object to be measured with measurement light, the apparatus comprising:
a light guiding member having a main surface, a back surface opposing the main surface, a side surface which intersects at least the back surface, and plural depressions in the main surface that act as light-emitting portions irradiating the object to be measured with measurement light; and
a light source outputting the measurement light to be introduced within the light guiding member through the side surface thereof,
wherein the plural light-emitting portions are located between the main surface and the back surface of the light guiding member, and
wherein the light guiding member has a structure such that the measurement light from the light source travels within at least a space between the plurality of light-emitting portions and the back surface of the light guiding member.

12. A light measurement apparatus, comprising:
the light irradiation apparatus according to claim 11, and
a microplate having a main surface on which plural wells each accommodating an object to be measured are two-dimensionally arranged and a back surface opposing the main surface, the microplate being arranged so as to directly face the main surface of the light guiding member of the light irradiation apparatus.

13. The light irradiation apparatus according to claim 11, wherein each of the plural light emitting portions includes one or more depressions each extending from the main surface toward the back surface of the light guiding member and having an opening on the main surface, and
wherein the measurement light, inputted into the light guiding member from the side surface thereof, is refracted and reflected at the side surface of each of the depressions, and then outputted from the opening of each of the depressions.

14. The light irradiation apparatus according to claim 13, wherein each of the depressions is a columnar depression.

15. The light irradiation apparatus according to claim 14, wherein each of the depressions has a flat bottom surface.

16. The light irradiation apparatus according to claim 15, wherein the bottom surface of each of the depressions is mirror-finished.

17. The light irradiation apparatus according to claim 13, wherein each of the depressions has a flat bottom surface.

18. The light irradiation apparatus according to claim 17, wherein the bottom surface of each of the depressions is mirror-finished.

19. The light irradiation apparatus according to claim 11, wherein each of the plural light emitting portions is located within the light guiding member while being apart from the side surface thereof.

20. A light measurement apparatus for measuring light from a microplate provided with plural wells each accommodating an object to be measured, the light measurement apparatus comprising:
a light guiding member having a main surface, a back surface opposing the main surface, a side surface which intersects at least the back surface, and a depression that acts as a light-emitting portion irradiating the microplate with measurement light;
a light source outputting the measurement light to be introduced within the light guiding member through the side surface thereof; and
a detector detecting the light from the microplate through the back surface of the light guiding member,
wherein the light-emitting portion is located between the main surface and the back surface of the light guiding member, and the detector is arranged so that the back surface of the light guiding member is located between the detector and the light-emitting portion.

21. The light measurement apparatus according to claim 20, wherein the light-emitting portion includes one or more depressions each extending from the main surface toward the back surface of the light guiding member and having an opening on the main surface.

22. The light measurement apparatus according to claim 21, further comprising a light source apparatus having: plural light sources including the light source: a filter; and a frame,
wherein the plural light sources are held by the frame while the plural light sources are arranged along the side surface of the light guiding member, and
wherein the filter is arranged between the side surface of the light guiding member and the plural light sources.

23. The light measurement apparatus according to claim 22, wherein the plural light sources includes at least two kinds of LEDs outputting light with wavelengths different from each other.

24. The light measurement apparatus according to claim 23, wherein the light source outputs the measurement light into the light guiding member through part of the side surface of the light guiding member, the part of the side surface corresponding a region between the light-emitting portion and the back surface of the light guiding member.

25. The light measurement apparatus according to claim 21, wherein the bottom surface of each of the depressions is mirror-finished.

26. The light measurement apparatus according to claim 21, wherein each of the depressions is a columnar depression.

27. The light measurement apparatus according to claim 21, wherein each of the depressions is a prism-shaped depression.

28. The light measurement apparatus according to claim 21, wherein each of the depressions is a trapezoid-shaped depression.

29. The light measurement apparatus according to claim 20, wherein the light emitting portion is located within the light guiding member while being apart from the side surface thereof.

30. The light measurement apparatus according to claim 29, wherein each of the main surface and back surface of the light guiding member is mirror-finished.

31. The light measurement apparatus according to claim 29, further comprising a light source apparatus having: plural light sources including the light source; a filter; and a frame,
wherein the plural light sources are held by the frame while the plural light sources are arranged along the side surface of the light guiding member, and
wherein the filter is arranged between the side surface of the light guiding member and the plural light sources.

32. The light measurement apparatus according to claim 31, wherein the plural light sources includes at least two kinds of LEDs outputting light with wavelengths different from each other.

* * * * *